(12) United States Patent
Tcheng

(10) Patent No.: US 11,690,553 B2
(45) Date of Patent: *Jul. 4, 2023

(54) MULTIMODAL BRAIN SENSING LEAD

(71) Applicant: NeuroPace, Inc., Mountain View, CA (US)

(72) Inventor: Thomas K. Tcheng, Pleasant Hill, CA (US)

(73) Assignee: NeuroPace, Inc., Mountain View, CA (US)

( * ) Notice: Subject to any disclaimer, the term of this patent is extended or adjusted under 35 U.S.C. 154(b) by 261 days.

This patent is subject to a terminal disclaimer.

(21) Appl. No.: 17/313,866

(22) Filed: May 6, 2021

(65) Prior Publication Data

US 2021/0259607 A1     Aug. 26, 2021

Related U.S. Application Data

(60) Continuation of application No. 16/442,424, filed on Jun. 14, 2019, now Pat. No. 11,026,617, which is a
(Continued)

(51) Int. Cl.
*A61B 5/291* (2021.01)
*A61N 1/36* (2006.01)
(Continued)

(52) U.S. Cl.
CPC ............ *A61B 5/291* (2021.01); *A61B 5/0006* (2013.01); *A61B 5/0031* (2013.01); *A61B 5/0205* (2013.01); *A61B 5/0261* (2013.01); *A61B 5/14553* (2013.01); *A61B 5/165* (2013.01); *A61B 5/316* (2021.01); *A61B 5/4082* (2013.01); *A61B 5/4094* (2013.01); *A61B 5/4839* (2013.01); *A61B 5/6868* (2013.01); *A61N 1/025* (2013.01); *A61N 1/0531* (2013.01); *A61N 1/0534* (2013.01); *A61N 1/36064* (2013.01); *A61N 1/36067* (2013.01); *A61N 1/36082* (2013.01); *A61N 1/36132* (2013.01);
(Continued)

(58) Field of Classification Search
None
See application file for complete search history.

(56) References Cited

U.S. PATENT DOCUMENTS 4,628,934 A   12/1986 Pohndorf
5,411,532 A   5/1995 Mortazavi
(Continued)

*Primary Examiner* — Carl H Layno
*Assistant Examiner* — Manolis Pahakis
(74) *Attorney, Agent, or Firm* — Loza & Loza, LLP; David S. Sarisky

(57) ABSTRACT

A medical lead with at least a distal portion thereof implantable in the brain of a patient is described, together with methods and systems for using the lead. The lead is provided with at least two sensing modalities (e.g., two or more sensing modalities for measurements of field potential measurements, neuronal single unit activity, neuronal multi unit activity, optical blood volume, optical blood oxygenation, voltammetry and rheoencephalography). Acquisition of measurements and the lead components and other components for accomplishing a measurement in each modality are also described as are various applications for the multimodal brain sensing lead.

12 Claims, 19 Drawing Sheets

Related U.S. Application Data continuation of application No. 15/478,168, filed on Apr. 3, 2017, now Pat. No. 10,390,721, which is a division of application No. 13/673,312, filed on Nov. 9, 2012, now Pat. No. 10,123,717.

(60) Provisional application No. 61/558,382, filed on Nov. 10, 2011.

(51) Int. Cl.
| | |
|---|---|
| *A61B 5/00* | (2006.01) |
| *A61B 5/026* | (2006.01) |
| *A61B 5/1455* | (2006.01) |
| *A61B 5/16* | (2006.01) |
| *A61N 1/05* | (2006.01) |
| *A61B 5/316* | (2021.01) |
| *A61B 5/0205* | (2006.01) |
| *A61N 1/02* | (2006.01) |

(52) U.S. Cl.
CPC ........ *A61N 1/36139* (2013.01); *A61B 5/7278* (2013.01); *A61B 2562/028* (2013.01); *A61B 2562/0209* (2013.01); *A61B 2562/0285* (2013.01); *A61B 2562/046* (2013.01); *A61B 2562/063* (2013.01)

(56) References Cited

U.S. PATENT DOCUMENTS

| | | | |
|---|---|---|---|
| 5,593,430 A | 1/1997 | Renger | |
| 5,999,848 A | 12/1999 | Gord et al. | |
| 6,129,685 A | 10/2000 | Howard | |
| 6,223,081 B1 | 4/2001 | Kerver | |
| 6,266,567 B1 | 7/2001 | Ishikawa et al. | |
| 6,343,226 B1 | 1/2002 | Sunde et al. | |
| 6,366,813 B1 | 4/2002 | DiLorenzo | |
| 6,473,653 B1 | 10/2002 | Schallhorn et al. | |
| 6,606,521 B2 | 8/2003 | Paspa et al. | |
| 6,793,670 B2 | 9/2004 | Osorio et al. | |
| 6,810,285 B2* | 10/2004 | Pless ............... | A61B 5/7246 600/544 |
| 7,277,748 B2* | 10/2007 | Wingeier ............ | A61B 5/369 600/544 |
| 7,285,118 B1 | 10/2007 | Lozano | |
| 7,630,078 B1* | 12/2009 | Nabutovsky ....... | A61N 1/36557 356/392 |
| 7,819,812 B2 | 10/2010 | John et al. | |
| 7,974,696 B1* | 7/2011 | DiLorenzo ........... | A61B 5/4082 607/45 |
| 8,024,045 B2 | 9/2011 | Carlton | |
| 8,175,668 B1* | 5/2012 | Nabutovsky ....... | A61N 1/36557 600/326 |
| 8,600,519 B2 | 12/2013 | Stevenson et al. | |
| 8,774,937 B2 | 7/2014 | Mercanzini | |
| 8,788,064 B2* | 7/2014 | Mercanzini ............ | A61B 17/34 607/45 |
| 9,980,645 B1 | 5/2018 | Durand et al. | |
| 2002/0109621 A1 | 8/2002 | Khair et al. | |
| 2002/0143258 A1 | 10/2002 | Weiner et al. | |
| 2003/0083724 A1* | 5/2003 | Jog ...................... | A61N 1/0536 607/122 |
| 2003/0088303 A1 | 5/2003 | Goode | |
| 2003/0093130 A1 | 5/2003 | Stypulkowski | |
| 2003/0195602 A1* | 10/2003 | Boling ................. | A61N 1/0539 607/122 |
| 2004/0030258 A1 | 2/2004 | Williams et al. | |
| 2004/0193021 A1* | 9/2004 | Zdeblick ................ | A61B 5/036 977/932 |
| 2005/0021104 A1* | 1/2005 | DiLorenzo ......... | A61N 1/36082 607/45 |
| 2005/0119703 A1* | 6/2005 | DiLorenzo ......... | A61N 1/36082 607/45 |
| 2005/0143790 A1* | 6/2005 | Kipke ...................... | A61B 5/24 607/60 |
| 2005/0240242 A1* | 10/2005 | DiLorenzo ........... | A61N 1/3605 607/45 |
| 2006/0079740 A1 | 4/2006 | Silver et al. | |
| 2006/0129204 A1 | 6/2006 | Pless et al. | |
| 2006/0129205 A1* | 6/2006 | Boveja ................. | A61N 1/3605 607/45 |
| 2006/0173494 A1 | 8/2006 | Armstrong et al. | |
| 2007/0123765 A1 | 5/2007 | Hetke | |
| 2007/0167991 A1* | 7/2007 | DiLorenzo ............ | A61B 5/4082 607/45 |
| 2007/0213783 A1* | 9/2007 | Pless ...................... | A61N 5/0622 607/42 |
| 2007/0265692 A1 | 11/2007 | Koop et al. | |
| 2008/0114417 A1* | 5/2008 | Leyde ................. | A61N 1/36082 607/60 |
| 2008/0147135 A1 | 6/2008 | Hareland | |
| 2008/0176271 A1 | 7/2008 | Silver | |
| 2008/0269777 A1* | 10/2008 | Appenrodt ........... | A61N 1/0529 606/130 |
| 2009/0012446 A1 | 1/2009 | Cui | |
| 2009/0088812 A1* | 4/2009 | Wulfman ................ | A61N 1/056 607/9 |
| 2009/0163981 A1 | 6/2009 | Stevenson et al. | |
| 2009/0192572 A1 | 7/2009 | Dal Molin et al. | |
| 2009/0204193 A1 | 8/2009 | Kokones et al. | |
| 2009/0228071 A1 | 9/2009 | Bourget | |
| 2009/0264899 A1* | 10/2009 | Appenrodt ............. | A61B 90/11 901/41 |
| 2010/0081914 A1* | 4/2010 | Waynik ................ | A61B 34/20 600/407 |
| 2010/0106227 A1 | 4/2010 | Min et al. | |
| 2010/0204766 A1 | 8/2010 | Zdeblick et al. | |
| 2010/0210958 A1 | 8/2010 | Manwaring et al. | |
| 2010/0312128 A1 | 12/2010 | Karst et al. | |
| 2010/0312298 A1 | 12/2010 | Pontiga et al. | |
| 2011/0054583 A1* | 3/2011 | Litt ...................... | A61N 1/0553 600/377 |
| 2011/0112381 A1* | 5/2011 | Sun ...................... | A61B 5/0205 600/300 |
| 2011/0112590 A1 | 5/2011 | Wu et al. | |
| 2011/0270362 A1 | 11/2011 | Goedeke et al. | |
| 2012/0059430 A1* | 3/2012 | Pless ...................... | A61B 5/369 607/45 |
| 2012/0101545 A1 | 4/2012 | Wahlstrand et al. | |
| 2012/0203316 A1 | 8/2012 | Moffitt et al. | |
| 2012/0245481 A1 | 9/2012 | Blanco | |
| 2013/0072775 A1 | 3/2013 | Rogers | |
| 2013/0172774 A1 | 7/2013 | Crowder et al. | |
| 2015/0164401 A1 | 6/2015 | Toth | |
| 2015/0224326 A1 | 8/2015 | Toth | |
| 2015/0289929 A1 | 10/2015 | Toth | |
| 2018/0185651 A1 | 7/2018 | Astrom et al. | |

* cited by examiner

```
seconds 0000000001111111111222222222233333333334444444444555555555 6
        1234567890123456789012345678901234567890123456789012345678 90
PD      AAAAAAAAAAAAAAA
L805    AAAAAAAAAAAAAAA
L630    AAAAAAAAAAAAAAAAAAA
PD                     BBBBBBBBBBBBB
L805                   BBBBBBBBBBBBB
L630                   BBBBBBBBBBBBB
PD                                  CCCCCCCCCCCCCC
L805                                CCCCCCCCCCCCCC
L630                                CCCCCCCCCCCCCC
PD                                                 DDDDDDDDDDDDDD
L805                                               DDDDDDDDDDDDDD
L630                                               DDDDDDDDDDDDDD
```

FIG. 18

TABLE 2

| | 1 minute |
|---|---|
| FP | 250 samples/second |
| SUA/MUA | 5000 samples/second |
| Optical | 20 samples/second |
| Voltammetry | 1 sample/minute |
| REG | 1 sample/minute |

FIG. 21A

TABLE 3

| | 1 minute |
|---|---|
| FP | 250 samples/second |
| SUA/MUA | 5000 samples/second |
| Optical | 20 samples/second |
| Voltammetry | 1 sample/minute |
| REG | 1 sample/minute |

FIG. 21B

MULTIMODAL BRAIN SENSING LEAD

CROSS-REFERENCE TO RELATED APPLICATIONS

This application is a continuation of U.S. application Ser. No. 16/442,424, titled "Multimodal Brain Sensing Lead," filed Jun. 14, 2019, which issued as U.S. Pat. No. 11,026,617, which is a continuation of U.S. application Ser. No. 15/478,168, titled "Multimodal Brain Sensing Lead," filed Apr. 3, 2017, now U.S. Pat. No. 10,390,721 issued Aug. 27, 2019, which is a divisional of U.S. application Ser. No. 13/673,312, titled "Multimodal Brain Sensing Lead," filed Nov. 9, 2012, now U.S. Pat. No. 10,123,717 issued Nov. 13, 2018, which claims the benefit of U.S. Provisional Application Ser. No. 61/558,382, filed on Nov. 10, 2011, each of which is expressly incorporated by reference herein in its entirety.

FEDERALLY SPONSORED RESEARCH OR DEVELOPMENT

The U.S. Government has a paid-up license in this invention and the right in limited circumstances to require the patent owner to license others on reasonable terms as provided for by the terms of the Department of Commerce, National Institutes of Standards and Technology, Cooperative Agreement No. 70NANB7H7001.

FIELD OF THE INVENTION

The present technology relates generally to systems and methods for detecting neurological dysfunction and other conditions, and more particularly, to a system and method for acquiring measurements corresponding to activity in or near a brain in multiple sensing modalities.

BACKGROUND

Increasingly, implantable active medical device systems are being used or investigated for use in treatment protocols or other therapies for a variety of neurological conditions or disorders. For example, implantable active medical device systems are known that rely upon an implanted pulse generator (IPG) or neurostimulator in operable communication with one or more electrodes (such as via electrode-bearing leads) to deliver a form of electrical stimulation (e.g., charge-balanced pulsatile stimulation) to the neural tissue of a patient. The stimulating elements and the form of stimulation may be configured based on the specific application of the system.

For example, electrodes may be implanted at or near particular anatomical structures or in particular neural circuits in a patient's brain and the stimulation parameters (e.g., amplitude and duration) may be optimized for addressing the symptoms of a movement disorder such as Parkinson's disease (e.g., tremor or bradykinesia). Similarly, electrodes may be located at deep brain structures that are understood to be related to major depressive disorder (MDD) and the parameters governing the stimulation selected to alleviate the condition. Many other potential applications of neurostimulation are being explored for addressing a wide variety of conditions or disorders understood to have a neurological connection, ranging from gastrointestinal disorders like gastroesophageal reflux disease (GERD) and obesity to migraine headaches. Still other applications of implantable active medical device systems include encouraging recovery of the brain from stroke.

Active implantable medical device systems have been used in clinical trials for patients with epilepsy in which an implanted neurostimulator may be configured to monitor electrographic signals sensed on one or more channels using sensing elements (such as macroelectrodes) that are implanted in or on the patient's brain. The neurostimulator further may be configured to process the sensed signals and to recognize one or more patterns occurring in the signals. The neurostimulator may have a variety of tools or algorithms that can be programmed to recognize certain patterns or sequences or other combinations of patterns when they occur in the sensed signals as "events." A given event may be understood to be related in some way to the patient's epilepsy (e.g., an event may be categorized as a precursor to a seizure or as a "seizure onset" or as a fully developed seizure). Additionally, the neurostimulator may be configured to generate and deliver through one or more stimulation elements a form of electrical stimulation therapy whenever it detects a particular event or events. Since in this system the neurostimulator can be configured to respond to events by delivering stimulation, the system is referred to as a responsive neurostimulation system. Once such responsive neurostimulation system is manufactured under the tradename the "RNS SYSTEM" by NeuroPace, Inc.

In many implantable neurostimulator systems, one or more external components may be configured for selective communication with the implanted neurostimulator (e.g., using inductive telemetry). A "programmer" is the name commonly used to refer to one of these external components, and it is used by a patient's physician to initially program or to reprogram the operating parameters of the neurostimulator). A programmer also may be configured to assess a state or condition of the neurostimulator (e.g., whether the neurostimulator is enabled to deliver stimulation or how much remaining life there is on the neurostimulator's primary cell or rechargeable battery). If the neurostimulation system is a responsive one and therefore one that acquires anti/or stores information sensed from the patient, then the programmer may also be used to interrogate the neurostimulator as to data the neurostimulator either has stored or is receiving in real time corresponding to the sensed signals.

A "remote monitor" is the name commonly used to refer to another of these external components, and it is used by the patient to communicate with the neurostimulator and to accomplish some limited set of functions (e.g., to disable stimulation, to cause the neurostimulator to store a record corresponding to a sensed signal at a time when the patient subjectively believes an "event" or a seizure might be occurring, and to download data from the neurostimulator so that it can be directed to a centralized database where the patient's physician can review it and perhaps otherwise manipulate it).

Electrical stimulation thus is an established therapy for treating some neurological disorders and responsive electrical stimulation is an emerging therapy for treating epilepsy and may be useful in treating other disorders and conditions. In responsive neurostimulation, delivery of therapy is triggered in response to information acquired about a physiological condition of a particular location or locations in or on the patient's brain (e.g., field potential measurements acquired from electrodes implanted at or near what is understood to be a focus of epileptiform activity for the patient). It will be appreciated that the success of a particular electrical stimulation therapy, at least to some degree, may be related to the quality and quantity of the physiological information that is relied upon to trigger that therapy. Moreover, this is likely to be the case regardless of which neurological disorder or condition the therapy is intended to treat (e.g., epilepsy, migraine headaches, movement disorders, etc.).

BRIEF DESCRIPTION OF THE DRAWINGS

FIG. 18 is a graphical illustration of the timing that an oxygenation measurement modality of a multimodal brain sensing lead might use according to an embodiment.

FIG. 21A is a table, referred to herein as Table 2, that illustrates the timing of measurement acquisition for various sensing modalities over one minute.

FIG. 21B is a table, referred to herein as Table 3, that illustrates the timing of measurement acquisition for various sensing modalities over one minute.

Figure 1:
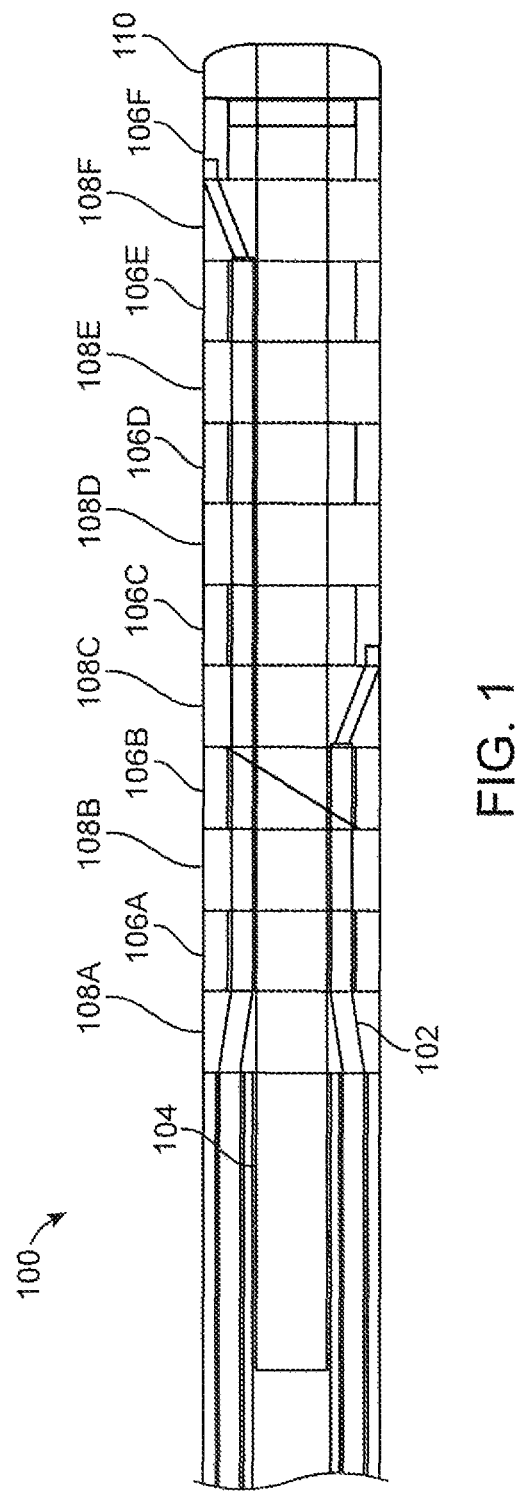
FIG. 1 is a side, partial sectional view of a proximal portion of a multimodal depth brain sensing lead according to an embodiment.

The drawings referred to in this description should not be understood stood as being drawn to scale unless specifically noted.

DESCRIPTION OF EMBODIMENTS

Various embodiments are described below, with reference to detailed illustrative embodiments, in the context of an implantable medical lead with multimodal sensing capability. It will be apparent from the description provided herein that the devices, systems, and methods can be embodied in a wide variety of forms. Consequently, the specific structural and functional details disclosed herein are representative and do not limit the scope of embodiments of the present technology.

Overview

A multimodal brain sensing lead is an implantable probe designed to collect physiological measurements using multiple sensing modalities all from a local region in a patient's brain. The timing of each physiological measurement may be multiplexed with the other physiological measurements, for example, so that all the measurements are acquired at close to the same time (to approximate concurrent sensing in multiple modes). The sensing modalities may include one or more of the following: (1) neuronal field potential (FP) measurements; (2) neuronal single unit activity (SUA) measurements; (3) neuronal multi unit activity (MUA) measurements; (4) rheoencephalography (REG) measurements; (5) neurochemical and pharmaceutical voltammetric (VM) measurements; (6) optical blood volume (OBV) measurements; and (7) optical blood oxygenation (OBO) measurements.

Desirably, the sensing modalities are implemented on the lead in a way that is conducive to having the lead remain in the patient's brain chronically, as opposed to acutely in, for example, a hospital setting. Implementing multiple sensing modalities on a single brain lead for acquiring localized physiological data chronically may be expected to result in excellent long-term visibility into physiological changes within the human brain.

Generally, neuronal field potential measurements describe the activity of large populations of neurons near the sensing electrodes. This activity may be used to detect pathological neurological events such as epileptic seizures and migraine. Neuronal single unit activity measurements describe the firing rates and patterns of single neurons. Neuronal multi unit activity measurements describe the firing rates and patterns of small local populations of neurons. While single unit activity measurements and multi unit activity measurements may be acquired using the same components on a multimodal brain sensing lead, and in fact this is the case in the embodiments described herein, each is considered a separate and distinct modality.

Certain single unit activity and multi unit activity firing patterns and rates are understood to be indicative of pathological states such as Parkinsonian tremor and subthalamic disinhibition. The relationship between single unit activity, multi unit activity and field potential measurements may be used to determine whether individual neurons or local populations of neurons are firing in a coordinated manner relative to a larger population of neurons.

Voltammetry measurements reflect concentrations of oxidizable and reducible drugs and neurochemicals. Neurochemicals may include neurotransmitters such as serotonin, dopamine, epinephrine and norepinephrine. Neurochemicals also may include other signaling molecules such as nitric oxide and hormones. Additionally, oxygen and hydrogen ions (i.e., pH) are neurochemicals that reflect metabolism and can be measured using voltammetry.

Drugs that may be measured using voltammetry include L-DOPA (brand name Sinemet), which is used to treat Parkinson's disease, and fluoxetine (brand name Prozac), which is a serotonergic drug used to treat mental disorders such as depression, obsessive compulsive disorder (OCD), eating disorders and panic attacks. These measurements can be used to measure drug levels directly at a therapeutic target, as a functional assay of the drug's effect on the release of neurochemicals. Voltammetric measurements also may be used to assay the physiological release of neurochemicals important in certain diseases such as movement disorders and depression.

Optical blood volume (OBV) and optical blood oxygenation (OBO) measurement methods can be used to measure hemodynamic variables, including blood volume, blood oxygenation, and heart rate. These methods use wavelengths that are specifically absorbed by oxygenated and deoxygenated hemoglobin. Additionally, blood flow can be estimated from optical blood volume measurements, since when blood flow increases, the relative ratio of blood volume to tissue increases. As was the case with the single unit activity measurement modality and the multi unit activity measurement modality, the optical blood volume measurement modality is considered to be a modality that is separate and distinct from the optical blood oxygenation measurement modality. This is the case even though both of the optical blood volume measurement modality and the optical blood oxygenation measurement modality may be accomplished using the same components on the multimodal brain sensing lead as, in fact, is the case with embodiments of a multimodal brain sensing lead described herein.

It likely is advantageous to measure hemodynamic variables in the same vicinity as the other physiological variables measurable by the multimodal brain sensing lead at least for the reason that a combination of diverse physiological measurements is likely to provide a more complete description of the physiological state of the tissue than is any one variable alone.

Hemodynamic variables vary between regions of the body and brain depending on local variables such as disease state and metabolic activity. Blood flow and blood oxygenation are important in diseases such as epilepsy, depression and migraine. For example, abnormal blood flow can be associated with seizures and with migraine aura and headache, and abnormal blood flow in limbic and cortical regions can be associated with major depression.

Rheoencephalography is the measurement of tissue impedance using electrical waveforms. Rheoencephalography can provide a measure of combined neuronal activity and blood flow. Rheoencephalography measurements are correlated with blood flow because blood has a lower electrical resistance than brain tissue. For example, when blood flow increases in a brain area, the blood vessels increase in diameter, resulting in an increased blood volume-to-brain tissue ratio. Because blood, has a lower electrical resistance than brain tissue, the electrical impedance through the area with increased blood flow is decreased.

Rheoencephalography measurements are also correlated with neuronal activity, because neurons decrease in volume when they become more active, causing increased intercellular space and lower electrical impedance. For example, when neurons in a particular brain area become active, these neurons shrink slightly, thus increasing the ratio of extracellular fluid to neuronal cell volume. This leads to decreased electrical impedance because extracellular fluid has lower impedance than neuronal cell bodies. Since rheoencephalography combines blood volume and electrophysiological metrics, it can be used to corroborate both hemodynamic and electrophysiological measurements. It is also possible that rheoencephalography measurements may be correlated in other clinically useful ways with disease symptoms and pathologies.

The information from multiple sensing modalities provided by embodiments may enable a clinician to more accurately characterize disease states, assess responses to therapeutic interventions, and make better informed adjustments to a patient's therapy. When a multimodal brain sensing lead according to embodiments is used to acquire different types of information over time, the information can beneficially provide numerous opportunities to adjust therapy based on the type, magnitude, and temporal patterns of observed physiological signs. For example, abnormal neuronal activity or blood flow changes might change, quite often in an independent manner, but the coincidence of both signs might signal a clinically relevant event and be used to trigger therapy delivery. Therapy can be fine tuned based on multimodal information, even without an understanding of its causal relationship to the patient's state. Specifically, signs that would otherwise be unobservable can be monitored and/or relationships, the significance of which may not be well understood, can be used to inform a patient's treatment with less reliance on patient-reported symptoms and externally observable signs.

Additionally, when embodiments of the multimodal brain sensing lead are used as part of a closed-loop, responsive therapy implantable delivery system, and numerous opportunities become available to deliver therapy based on the timing and concordance of observed physiological signs. For example, abnormal neuronal activity or blood flow changes might occur independently quite often, but the coincidence of both signs might signal a clinically relevant event and be used to trigger therapy delivery.

The discussion will begin with a summary of various embodiments. Then a description of embodiment characteristics will follow. The discussion continues with a more particularized description of the multimodal lead, including gross dimensions and various components. The discussion then turns to a description of measurement acquisition, measurement acquisition timing and uses of acquired measurements. Finally, clinical examples are discussed.

Characteristics of Embodiments

Embodiments of the multimodal brain sensing lead include chronically implantable miniaturized sensors that are configured for multimodal sensing from a localized brain area with multiplexed timing. Embodiments of the multimodal brain sensing lead may include one or more of the following features: (1) multimodal sensing using sensors carried by a single probe or lead to allow highly localized monitoring; (2) sensing using the various modalities at around the same time or at coordinated times; and (3) MRI safety.

Chronic Implantability

Two major challenges are associated with providing a brain lead that can be chronically implanted. First, for the lead to be implantable, it must be made of materials that are biocompatible and safe to the patient. All of the materials included in embodiments of the multimodal brain sensing lead described here are generally considered to be safe and biocompatible. More particularly, the materials may include: silicone; a 90% platinum, 10% iridium alloy (a.k.a. PtIr); polyether ether ketone (a.k.a. PEEK); vitreous carbon (a.k.a. glassy carbon); glass; sapphire; titanium; tantalum; biocompatible epoxy; and ethylene tetrafluoroethylene (a.k.a. ETFE).

Second, for sensors to be implantable, they must be designed and constructed in such a way that they can function robustly inside the body, and desirably will continue to function for the life of the patient, without having to be replaced. Embodiments of the multimodal brain sensing lead and the sensors used in connection therewith include design features that support chronic implantability. One such design feature is providing multiple, redundant transducers on the multimodal brain sensing lead for some or all of the different sensing modalities. This redundancy will allow an alternate transducer to be used if a primary transducer fails and/or allows the best of two or more measurements for a given modality to be selected.

When one of the modalities provided in embodiments is voltammetry, then another robustness feature is a durable design for the voltammetry electrodes. Traditional voltammetry electrodes for in vivo use are made of a single carbon fiber extending from the tapered tip of a glass micropipette. This traditional design can be quite fragile and thus likely impractical or otherwise unsuitable for long term (chronic) use. Embodiments of the multimodal brain sensing lead that are configured for the voltammetry modality may use the disk-shaped end of a glassy carbon cylinder as a voltammetry electrode. Glassy carbon is extremely durable and suitable for a chronic recording application.

Alternatively, ultrananocrystalline diamond (UNCD) coated metal, which is also very durable and suitable for voltammetry, may be used for the voltammetry electrode.

Other features that may be provided according to embodiments for one or more sensing modalities and which are expected to contribute to robustness and durability include electrical isolation of sensor components from each other and from other elements of the leads (e.g., conductors); and the use of non-corroding materials, hermetic seals and feedthroughs. These features are elaborated upon in the description below.

Miniaturized Sensors

The optical and microelectrode sensors described below and according to embodiments are highly miniaturized and designed to fit into the very limited space available in an implantable lead. The optical sensor includes two LEDs and a photodiode, each of which is specifically selected, arranged and packaged so that they fit into a small space. In an embodiment, the dimensions of this small space are approximately 1.5×0.5×0.3 mm. The wiring that connects the sensor to the electronics module is designed to accommodate the small space available and facilitate manufacturing and assembly.

The microelectrode module has also been designed for manufacturability and for easy incorporation into the lead. This design is simple and elegant in that no welding of contacts is required. Especially in embodiments in which glassy carbon is used for a microelectrode, this material cannot be welded because it is too hard and inert for welding. The microelectrodes are press fit through a hole in the side of a PEEK cylinder and the sharp metal tip of each microelectrode—for a glassy carbon microelectrode, this is the pointed end of the proximal end of the electrode (as will be described below)—penetrates and deforms a metal contact on the electronics module, thus making a secure connection. An alternative to glassy carbon is ultrananocrystalline diamond-coated tantalum, platinum-indium, or other metal.

Multimodal Sensing

Embodiments are specifically designed for multimodal sensing. Multimodal sensing is the combined acquisition of two or more of: (1) neuronal field potential measurements; (2) neuronal single unit activity measurements; (3) neuronal multi unit activity measurements; (4) rheoencephalography measurements; (5) neurochemical and pharmaceutical voltammetric measurements; (6) optical blood volume measurements; and (7) optical blood oxygenation measurements. Multimodal sensing is desirable at least for the reason that it provides a more complete description of physiological activity than is achievable with any single modality. Most diseases and disorders of the brain involve a combination of abnormal neuroelectric, neurochemical, and hemodynamic activities.

Time Multiplexed Sensing

Embodiments are specifically designed for time multiplexed multimodal sensing. Time multiplexed sensing as used herein means the ability to collect multiple modalities of information at or about the same time. Time multiplexed sensing may be a desirable alternative to same-time sensing, since some sensing modalities cannot be used simultaneously. For example, if one component (e.g., a physical element) used in a first sensing modality is also used in a second sensing modality, the component may have to be shared by different sensing modalities.

Modalities that may share one or more components with other modalities include voltammetry, neuronal single unit activity, and neuronal multi unit activity sensing modalities. A voltammetry modality may be configured to use the same microelectrodes as a single unit activity modality and/or as a multi unit activity modality.

Additionally, time multiplexed sensing may be desirable to avoid situations in which one sensing modality interferes with another sensing modality or modalities. For example, if voltammetry and field potential measurements were undertaken simultaneously, then the waveform used to acquire the voltammetry measurement may be reflected somehow in the field potential measurement, such that the voltage changes sensed in the field potential measurement would to some degree be sensed simply because the voltammetry measurement was being acquired. In other words, the voltammetry modality may cause voltage changes in the tissue that would interfere with field potential measurements if both the voltammetry measurement and the field potential measurement were acquired simultaneously.

Time multiplexed sensing also is important because the convergence of information from multiple modalities over time is likely a better diagnostic indicator than information from any single modality. Depending on the specific combinations of sensing modalities, time multiplexed sensing may be simultaneous or interleaved.

Embodiments of a multimodal brain sensing lead meet several technical challenges. Specifically, the method of making measurements using each modality satisfies the following requirements: (1) making a measurement using one modality must not interfere with measurements of any other modalities; (2) measurements from each different modality provided via the lead must be made frequently enough to provide a clinically relevant description of ongoing physiological activity; (3) making measurements from all modalities must use a minimum of electrical power, so that battery life is maximized; and (4) measurements from all modalities must be safe.

Localized Monitoring

The multimodal brain sensing lead is specifically designed for localized monitoring of multiple physiological variables. The multimodal lead thus provides one way to monitor multiple modalities of physiological information at or about the same time from the same localized brain area. In embodiments, sensors for multiple different modalities are placed in close proximity to each other on the same probe or lead for optimal localization of the measured data. Localized monitoring of multiple physiological variables is important for describing physiological changes that are correlated in space as well as in time.

In addition to supporting chronic implantability, embodiments are provided with multiple sensors for each sensing modality so that within a modality, the sensor with the best signal may be monitored, and so that sensors in sub-optimal locations may be ignored. This redundancy can serve one or both purposes: (1) redundancy in case of failure and (2) selection of a sensor with the best signal. For example, under the circumstances of a particular lead implant and depending, on the desired signals, measurements from sensors or transducers that are physically situated adjacent a blood vessel or in the fluid of a brain ventricle may be sub-optimal. In this case, if an embodiment is provided with multiple instances of for example, a voltammetry sensor, then a measurement from a voltammetry sensor configuration not so close to the blood vessel may be preferred over a measurement from a voltammetry sensor configuration adjacent to the blood vessel. Additionally, embodiments with redundancy in the sensor configurations for a given modality may be leveraged in order to identify a location in the patient's brain from which the most clinically relevant activity may be measured. For example, choosing the most clinically relevant sensor configurations to use for a given modality on a given lead may involve comparing signals from sensor configurations for the same modality but located at different places along the same lead or located on different leads altogether.

MRI Safety

Embodiments of the multimodal sensing brain lead incorporate features that contribute to safety in an MRI field by minimizing the degree to which components in the distal portion of the lead heat when the patient is subjected to magnetic resonance imaging Heating in an implanted lead in an MRI field occurs because electromagnetic energy is absorbed by long wires in the lead (e.g., conductors) and is converted to heat at the macroelectrodes, which can damage brain tissue near the macroelectrodes. In some variations of implantable brain leads, electromechanical relays are used to physically disconnect the macroelectrode from the lead wires and prevent heating of the macroelectrodes and tissue damage. In embodiments of a multimodal brain sensing lead described here, an electronics module provided in the lead may contain an omnidirectional magnetic field detector configured to detect when a sufficiently strong magnetic field with characteristics indicative of an MRI system is present. When the MRI field is detected by the omnidirectional magnetic field detector, then this detection causes microelectromechanical relays in the lead (e.g., in an electronics module provided in the lead) to operate to disconnect the lead wires from the macroelectrodes. In this way, macroelectrode heating due to electromagnetic energy from an MRI system is discouraged.

Multimodal Depth Brain Sensing Lead

Gross Lead Dimensions

In one embodiment, the gross dimensions of an implantable multimodal depth brain sensing lead are about 44 cm in length, and round in cross section with a diameter of about 1.25 mm. However, it should be appreciated that the gross lead dimensions may be different than those specifically described herein. In one embodiment, the multimodal brain sensing lead consists of three major sections: a distal portion, which is surgically implanted at a desired location within the brain; an elongated lead body, and a proximal portion, which may either be connected to the housing of an internal host device implanted in the body, preferably the cranium, or to an external host device outside the body.

Proximal Portion of Multimodal Depth Brain Sensing Lead

The design of the proximal portion of the multimodal brain sensing lead facilitates chronic implantability through reliable connections to the proximal lead contacts, secure electrical connections, good electrical isolation, and durable construction. FIG. 1 is a side, partial sectional view of a proximal portion of a multimodal brain sensing lead 100, in accordance with an embodiment. The proximal portion 100 includes lead wires or conductors 102, a length of polyimide tubing 104, proximal lead contacts 106A, 106B, 106C, 106D, 106E, and 106F (hereinafter, "proximal lead contacts 106", unless otherwise noted), silicone spacers 108A, 108B, 108C, 108D, 108E, and 108F (hereinafter, "silicone spacers 108", unless otherwise noted), and a proximal end cap 110. In one embodiment, the number of lead wires or conductors 102 is six. In this embodiment, the six lead wires or conductors 102 are connected to the proximal lead contacts 106 that are threaded onto the length of the polyimide tubing 104 and separated from each other by the silicone spacers 108. The proximal lead contacts 106 couple with electrical contacts on a connector in the host device, facilitating the transfer of electrical signals through the lead. Four of the lead wires or conductors 102 that are connected to the four most distal lead contacts of the proximal lead contacts 106 are used for neuronal field potential recording and electrical stimulation, while the remaining two lead contacts of the proximal lead contacts 106 are used for the transmission of power and digital communication.

Figure 2:
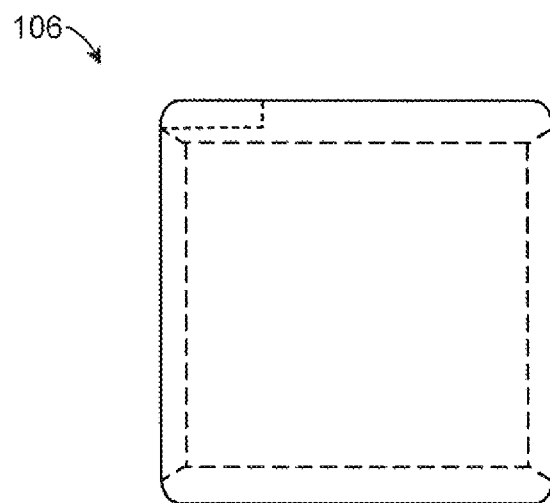
FIG. 2 is a cross-sectional view of a lead contact of FIG. 1.
Figure 3:
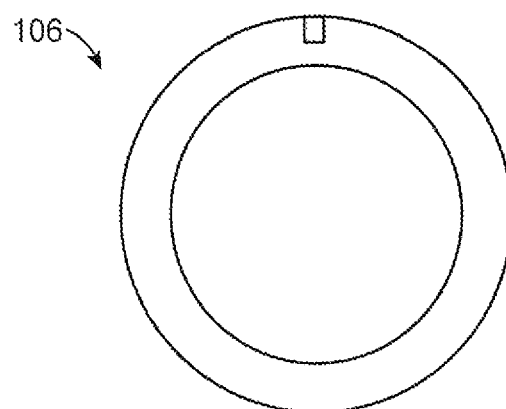
FIG. 3 is an end view of a lead contact of FIG. 1.

FIG. 2 is a cross-sectional view and FIG. 3 is an end elevational view of a proximal lead contact 106 of FIG. 1, in accordance with an embodiment. In one embodiment, the proximal lead contacts 106 are metal rings, made of a 90% platinum and a 10% iridium alloy (a.k.a. "PtIr"), that are about 1.5 mm long, with an outer diameter of about 1.25 mm and an inner diameter of about 0.9 mm. It should be noted, however, that the make up and dimensions of the proximal lead contacts 106 may have other make ups and dimensions than that described herein. The inner and outer edges of the cylinder ends, in one embodiment, are beveled at 45 degrees for about 0.025 mm. This sort of beveling eliminates sharp edges that might damage tissue, and facilitates over-molding of silicone between electrodes. In one embodiment, each proximal contact 106 has a groove that is about 0.10 mm wide and deep, and about 0.75 mm long that extends from the outer edge of the distal contact end, and that extends towards a proximal end of the proximal contacts 106. It should be noted that the groove may have dimensions other than that described herein. The groove is for attachment of a lead wire, such as lead wire or conductor 102. The proximal lead contacts 106 may be sequentially numbered 1-6 in distal-to-proximal order.

A multimodal brain sensing lead according to embodiments is formed from a length of polyimide tubing 104 that runs through the center of the proximal lead contacts 106 and silicone separators 108. The length of the polyimide tubing 104 may be about 23 mm long, 0.50 mm diameter, and characterized by a wall thickness of about 0.025. The polyimide tubing 104 serves to stiffen the proximal lead end 100, insulate the inner aspect of the proximal lead contacts 106 and protect the inner aspect of the proximal lead contacts 106 from damage, for example, by a stylet used to provide stiffness or rigidity to the lead while the lead is being implanted in the patient. It should be noted that the polyimide tubing 104 may be of any dimension that still enables the polyimide tubing 104 to function as described herein.

In one embodiment, five silicone spacers 108 separate six proximal lead contacts 106 from each other. For example, each spacer may be about 1.5 mm long and made of silicone that is molded over the lead wire(s) or conductor(s) 102 and polyimide tubing 108 and into the space between the proximal lead contacts 106. This silicone provides electrical insulation.

Figure 4:
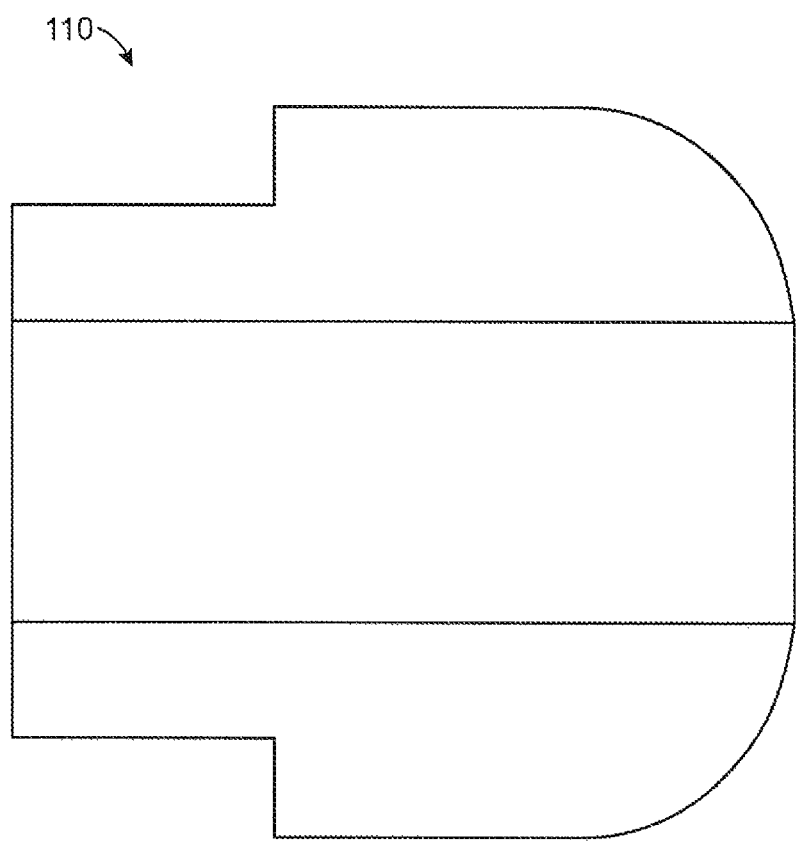
FIG. 4 is an enlarged side view of a proximal end cap that may be used with the proximal portion shown in FIG. 1.

FIG. 4 illustrates an enlarged side view of a proximal end cap 110 that is also shown in FIG. 1, in accordance with an embodiment. The proximal end cap 110 may be press-fit into the proximal end of the most proximal lead contact of the proximal lead contacts 106. In one embodiment, the proximal end cap 110 may be made of PtIr and cylindrical with an inner diameter of about 0.5 mm. In yet another embodiment, the proximal end of the proximal end cap 110 is about 1 mm long and 1.25 mm in diameter. The outer proximal edge of the proximal end cap 110 is rounded. In one embodiment, the distal end of the proximal end cap 110, which is press-fit into the most proximal contact, is about 0.5 mm long and about 0.9 mm in diameter.

Still referring to FIGS. 1-4, prior to lead implantation, in one embodiment, a stylet is inserted through the hole in the proximal end cap 110 into the central lumen of the lead. The stylet provides support for the lead and makes it semi-rigid while it is implanted in the brain. The stylet is removed after the lead is stereotactically positioned within the brain.

In one embodiment, six lead wires or conductors 102 run the length of the lead body. Each lead wire or conductor 102 may be about 0.1 mm in diameter and made of multistranded PtIr wire. Each lead wire may be coated with insulation (e.g., a layer of ethylene tetrafluoroethylene ETFE) insulation), resulting in a somewhat greater overall diameter. At the proximal lead end 109, the lead wires or conductors 102 are threaded between the polyimide tubing 104 and the inside of the proximal lead contacts 106. A proximal section of each lead wire of the lead wires or conductors 102 is stripped of insulation for about 0.5 mm, pressed into the groove of a proximal lead contact of the proximal lead contacts 106, and laser-welded into place, according to an embodiment. Each lead wire may be numbered 1-6 according to the proximal lead contact to which it is connected. At a distal portion of the lead, each lead wire 102 may be laser-welded to a connection point on an electronics module located in a distal portion of the lead according to an embodiment.

Lead Body

Figure 5A:
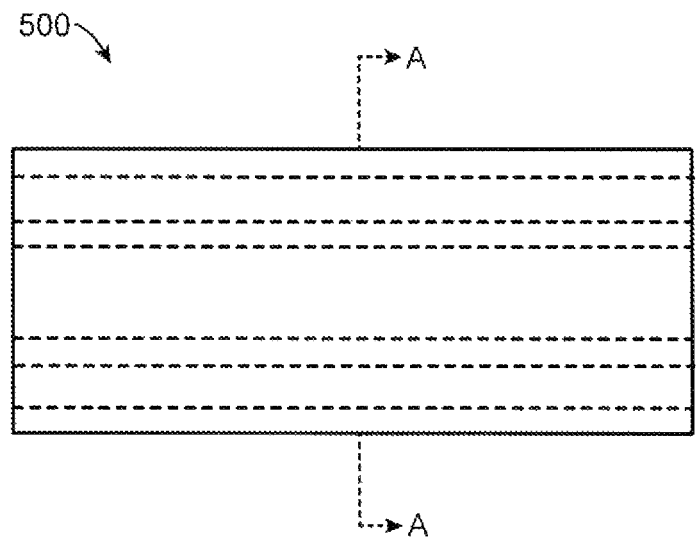
FIG. 5A is a side view of a portion of a multimodal sensing lead body according to an embodiment.
Figure 5B:
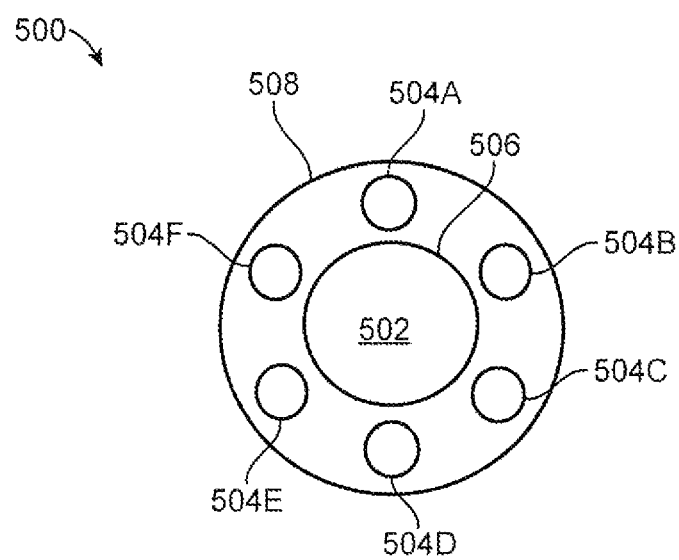
FIG. 5B is cross-sectional view taken along the line A-A of FIG. 5A.

FIG. 5B is a cross-sectional view of a lead body 500 taken along the line A-A of FIG. 5A, in accordance with an embodiment. In one embodiment, is a multi lumen tube of silicone with an outer diameter of about 1.25 mm. A central lumen 502 is about 0.5 mm in diameter. Six smaller lumens 504A, 504B, 504C, 504D, 504E, and 504F (hereinafter, "smaller lumens 504", unless otherwise noted), each of about 0.2 mm in diameter, surround the central lumen 502, according to an embodiment. These smaller lumens are positioned about midway between an outer edge 506 of the central lumen 502 and an outer edge 508 of the lead body 500, and are circularly arranged at 60 degree intervals around the center of the lead body 500. The six lead wires or conductors 102 run through the six smaller lumens 504. A stylet may be inserted into the central lumen 502 for use while the lead is being implanted in the patient and then removed. After the lead is implanted and the stylet has been removed, the central lumen 502 eventually fills with fluid. The multi lumen design and insulated lead wires or conductors 102 facilitate chronic implantability by providing good electrical isolation of the lead wires 102. Providing lead wires or conductors 102 that are multistranded contributes to good durability.

Distal Portion of Multimodal Depth Brain Sensing Lead

Figure 6:
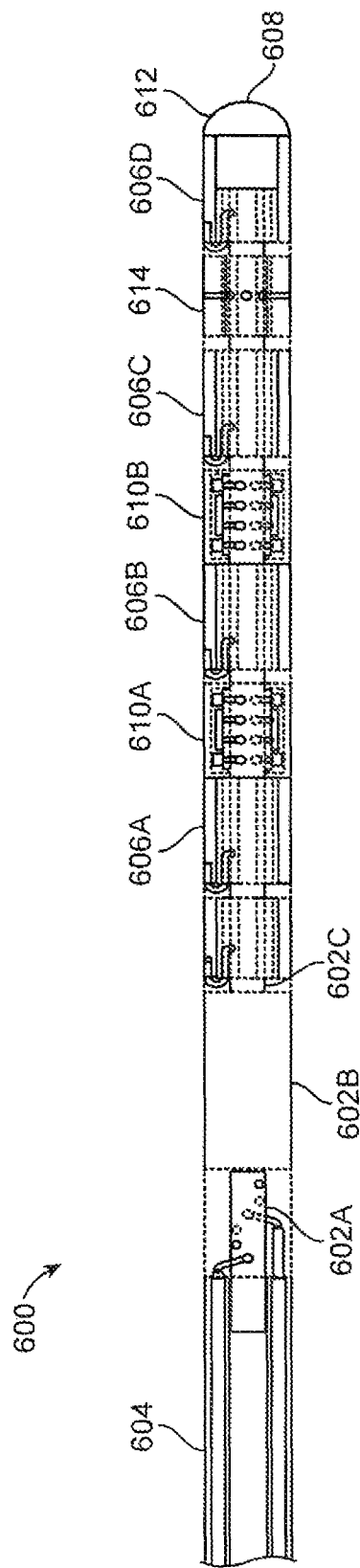
FIG. 6 is a side, partial sectional view of a distal portion of a multimodal deep brain sensing lead according to an embodiment.

FIG. 6 is a side, partial sectional view of a distal portion 600 of a multimodal depth brain sensing lead, according to an embodiment. The distal portion 600 includes: an electronics modules, including a first electronic module component 602A, a second electronics module component 602B and a third electronics module component 602C (hereinafter, "electronics module 602", unless otherwise noted) that connects to the six lead wires 102 at a proximal portion 604 of the distal portion 600; three kinds of transducers for seven different sensing modalities; macroelectrodes 606A, 606B, 606C and 606D (hereinafter, "macroelectrodes 606", unless otherwise noted) for the field potential measurement modality and the rheoencephalography measurement modality; optical assemblies 610A and 610B (hereinafter, "optical assemblies 610", unless otherwise noted) for the optical blood volume and optical blood oxygenation modalities; and a microelectrode assembly 614 for the voltammetry modality the neuronal single unit activity measurement modality and/or the neuronal multi unit activity measurement modality; a distal tip 612; and a distal end 608 of the distal portion 600. Together, the electronics module 602 and transducers service all of the sensing modalities.

Figure 7:
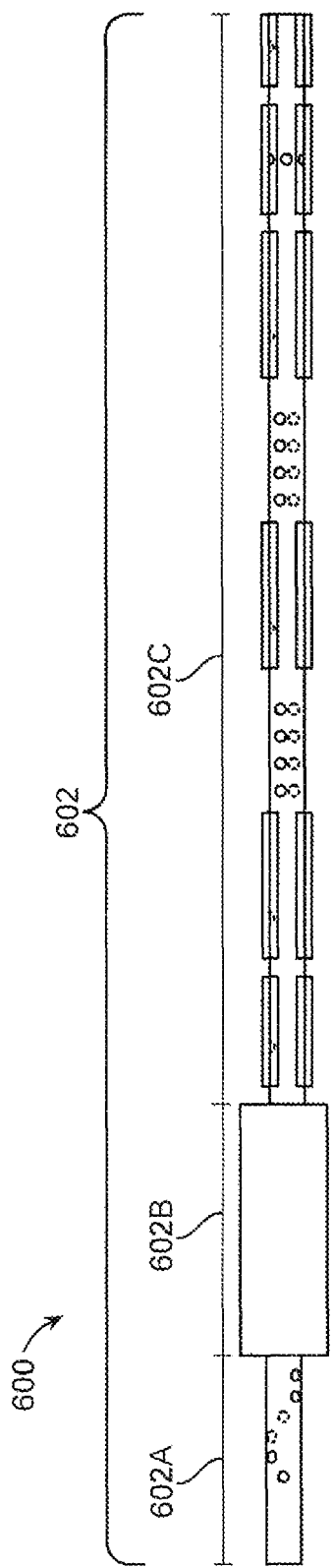
FIG. 7 is an enlarged view of an electronics module of FIG. 6.

FIG. 7 is an enlarged view of the electronics module 602 of FIG. 6, in accordance with an embodiment. The electronics module 602 consists of a main body 602B, a proximal shaft 602A, and a distal shaft 602C. The main body 602B, the proximal shaft 602A, and the distal shaft 602C are made of a nonconductive, biocompatible material, such as polyether ether ketone (a.k.a. PEEK), according to an embodiment. The design of the electronics module 602 is robust and durable, supporting chronic implantation as well as the miniaturized multimodal sensors.

Referring still to FIGS. 1-7, in one embodiment, the main body 602B is a PEEK cylinder about 2 mm long and about 1.25 mm in diameter. It contains electronic circuits that support the multiple sensing modalities. These electronics are hermetically packaged and connected via hermetic feedthroughs to electrical contacts on the proximal shaft 602A and the distal shaft 602A. Some specific electronics are described that may be used beneficially in embodiments are described below in the context of the methods used to acquire measurements for each sensing modality.

According to an embodiment, the proximal shaft 602A of the electronics module 602 is a PEEK cylinder about 3 mm long and about 0.5 mm in diameter, extending proximally from the main body 602B of the electronics module 602. The tip of the proximal shaft 602A is designed to be inserted about 1 mm into the central lumen 502 of the lead body 500. In one embodiment, the tip may be adhered in place by silicone that is molded around the portion of the proximal shaft 602A between the lead body 500 and the main body 602B of the electronics module 602. The silicone also serves to electrically isolate the exposed ends of the lead wires or conductors 102 that are laser-welded to contacts on the proximal shaft 602A. There are six electrical contacts on the proximal shaft 602A, centered at about 0.3 mm intervals from each other, starting 0.3 mm from the proximal end of the main body 602B. The electrical contacts are also centered at about 60 degree intervals from each other so that they are arranged in a spiral pattern along the proximal shaft 602A.

The six lead wires or conductors 102 are connected to the contacts on the proximal shaft 602A in the same proximal-to-distal order as they are connected to the proximal lead contacts 106 on the proximal portion 100 (of FIG. 1). That is, the most proximal contact on the proximal portion 100 is connected to the most proximal contact on the proximal shaft 602A of the electronics module 602, and so on and so forth. In an embodiment, the four most distal contacts are used for neuronal field potential recording. In some embodiments, where the multimodal brain sensing lead is also configurable to deliver a form of electrical stimulation to the patient (in addition to sensing physiological information from the patient), the four most distal contacts may also be used as electrodes through which electrical stimulation can be delivered, although typically not at the same time as a given contact is being used for sensing. The two most proximal contacts may be used for power and digital communication.

In an embodiment, the six lead wires or conductors 102 extend past the end of the multilumen tube of the lead body 500 for varying lengths of about 0.8 to 1.8 mm at about 0.3 mm intervals. Each lead wire or conductor 102 may be stripped of about 0.5 mm of insulation and their ends laser-welded to the electrical contacts on the proximal shaft 602A. Electrically conductive circuit paths within the proximal shaft 602A connect to the electronics package in the main body 60213. Their initial connections may be to microelectromechanical relays (not shown) which are controlled by electronic circuitry that detects an MM field and disconnects the lead wires 102 from the macroelectrodes 606 to reduce macroelectrode heating by electromagnetic MRI energy.

Figure 8:
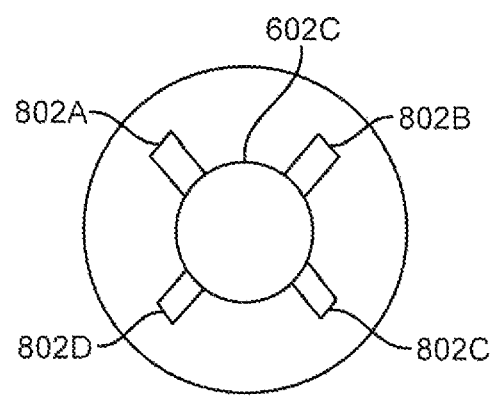
FIG. 8 is a cross-sectional view of a shaft associated with the electronics module of FIG. 7.

FIG. 8 is an enlarged end view of the distal shaft 602C of the electronics module 602 of FIG. 7. The distal shaft 602C may be formed from a PEEK cylinder about 15 mm long and about 0.5 mm in diameter that extends distally from the main body 602B of the electronics module 602. At the locations where macroelectrodes and a microelectrode assembly are positioned, there are four ridges, 802A, 802B, 802C, and 802D (hereinafter, "ridges 802", unless otherwise noted). Each ridge may be about 0.1 mm wide, about 0.18 mm tall and located at about 90 degree intervals from each other, according to an embodiment. Each ridge of the ridges 802 may be the same length as the macroelectrode or microelectrode assembly that fits over it. The ridges 802 serve to help position the macroelectrodes and microelectrode assembly during construction of the lead.

Electrically conductive circuit paths extend from the electronics package through moisture-proof hermetic seals into the proximal shaft 602A and the distal shaft 602C of the electronics module 602, and terminate in connection points for the attachment of lead wires or conductors 102, proximally, and macroelectrodes 606 (of FIG. 6), distally.

The transducers provided on a given instance of a multimodal brain sensing lead may include any or all the following: (1) macroelectrodes; (2) microelectrodes; (3) light emitters; and (4) photodetectors. The different sensing modalities use the different transducers as follows: (1) neuronal field potential measurements are made using macroelectrodes; (2) neuronal single unit activity measurements are made using microelectrodes; (3) neuronal multi unit activity measurements are also made using microelectrodes; (4) rheoencephalography measurements are made using macroelectrodes; (5) neurochemical and pharmaceutical voltammetric measurements are made using both macroelectrodes and microelectrodes; (6) optical blood flow and volume measurements are made using light emitters and photodetectors; and (7) optical blood oxygenation measurements are also made using light emitters and photodetectors.

Figure 9:
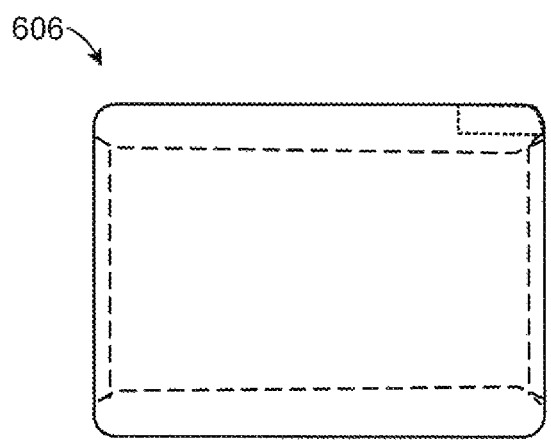
FIG. 9 is a side, partial sectional view of a macroelectrode which may be used with a multimodal brain sensing lead according to embodiments.
Figure 10:
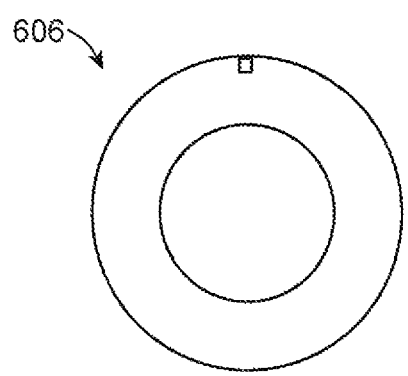
FIG. 10 is a cross-sectional view of the macroelectrode of FIG. 9.

FIGS. 9 and 10 are different views of a macroelectrode 606: FIG. 9 is a side, partial sectional view of a macroelectrode 606 and FIG. 10 is a cross-sectional view of a macroelectrode 606. In one embodiment, there are five macroelectrodes on a distal portion 600 of the multimodal brain sensing lead. Each macroelectrode 606 may be identified by the number of the lead wire or conductor 102 to which it is connected. In an embodiment of a multimodal depth brain sensing lead, each macroelectrode 606 is a PtIr ring with an outer diameter of, about 1.25 mm, and an inner diameter of about 0.9 mm Four of the macroelectrodes are about 2 mm long and used for neuronal field potential measurements, rheoencephalography measurements and delivering electrical stimulation, according to an embodiment. The fifth macroelectrode is about 1.5 mm long and is used as a counter or reference electrode for voltammetry and microelectrode recording, according to an embodiment. Each macroelectrode 606 may have a groove that is about 0.1 mm wide and deep and about 0.375 mm long that extends from the outer edge of the distal contact end, and towards the proximal end of the contact.

In some embodiments, macroelectrodes 606 are assembled onto the distal shaft 602C of the electronics module 602 in two steps. First, one end of an about 2 mm long, 0.1 mm diameter Par wire is laser-welded into the groove in a macroelectrode 606. Then the macroelectrode 900 is threaded onto the distal shaft 602C, groove first, and the other end of the wire is laser-welded to a contact point on the distal shaft 602C. Then the macroelectrode 900 is pushed over the welded contact on the distal shaft 602C and the wire is drawn tight. Silicone is injected into the space flanking each macroelectrode 606, also filling the space between the inside of each macroelectrode 606 and the distal shaft 602C.

Figure 11A:
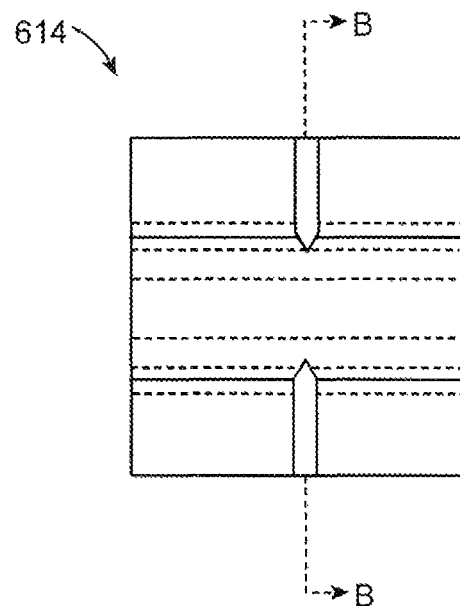
FIG. 11A is a side, partial sectional view of a microelectrode assembly which may be used with a multimodal brain sensing lead according to embodiments.
Figure 11B:
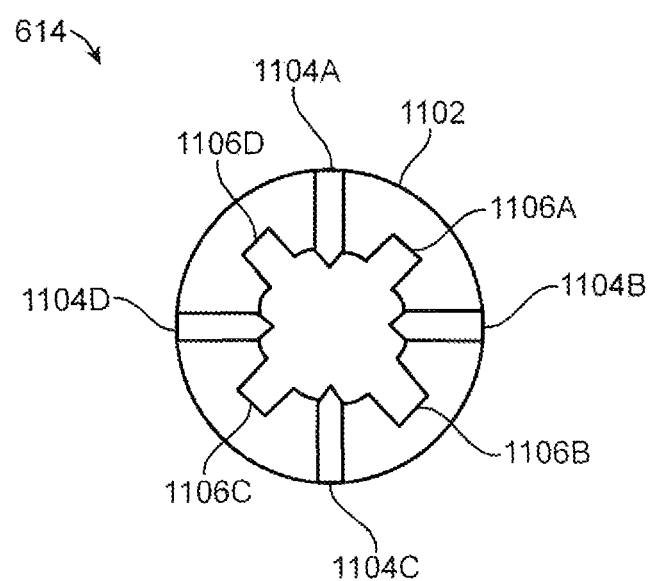
FIG. 11B is a cross-sectional view taken along the line B-B of the microelectrode assembly of FIG. 11A.

FIGS. 11A and 11B are views of a microelectrode assembly 614 of FIG. 6, in accordance with an embodiment. A microelectrode assembly 614 exists on the distal portion 600 of the multimodal brain sensing lead. Microelectrodes may be used for making neuronal single unit activity and neuronal multi unit activity measurements as well as for making voltammetry measurements. A microelectrode assembly 614 may consist of a ring-shaped assembly body 1102 with four cylindrical microelectrodes, 1104A, 11048, 1104C, and 1104D (hereinafter, "microelectrodes 1104", unless otherwise noted) embedded into its surface. The assembly body 1102 is made of a nonconductive, biocompatible material, such as PEEK, and is about a 1.5-mm long cylinder with an outer diameter of about 1.25 mm and an inner diameter of about 0.6 mm, in accordance with an embodiment. There may be four grooves, 1106A, 11068, 1106C, and 1106D (hereinafter, "grooves 1106", unless otherwise noted) in the inside of the cylinder at about 90 degree intervals from each other. Each groove of the grooves 1106 may be about 0.15 mm wide and 0.15 mm deep. The grooves fit over the ridges on the distal shaft 602C of the electronics module 602 and aid in positioning of the microelectrode assembly 614 during lead construction.

The microelectrodes 1104 may be made of a biocompatible material suitable for both voltammetry and neural (single or multi) unit activity recording, such as glassy carbon. Alternatively, a material such as tantalum coated with ultrananocrystalline diamond may be used. A typical microelectrode 1104 may be about 0.425 mm long and about 0.1 mm in diameter, with one pointed end, in one embodiment. The microelectrodes 1104 are positioned midway between the two ends of the assembly body 1102 and arranged circularly around its perimeter at about 90 degree intervals, midway between the grooves, in one embodiment. The tapered end of each microelectrode of the microelectrodes 1104 is pressed into about a 0.1 mm hole in the assembly body 1102 so that the outer end of the microelectrodes 1104 are flush with the outer surface of the assembly body 1102, in accordance with an embodiment. Each microelectrode of the microelectrodes 1104 may be located directly over an electrical contact point on the distal shaft 602C. When the microelectrode is pressed into its hole, it slightly deforms the contact, making a secure electrical connection.

Figure 12:
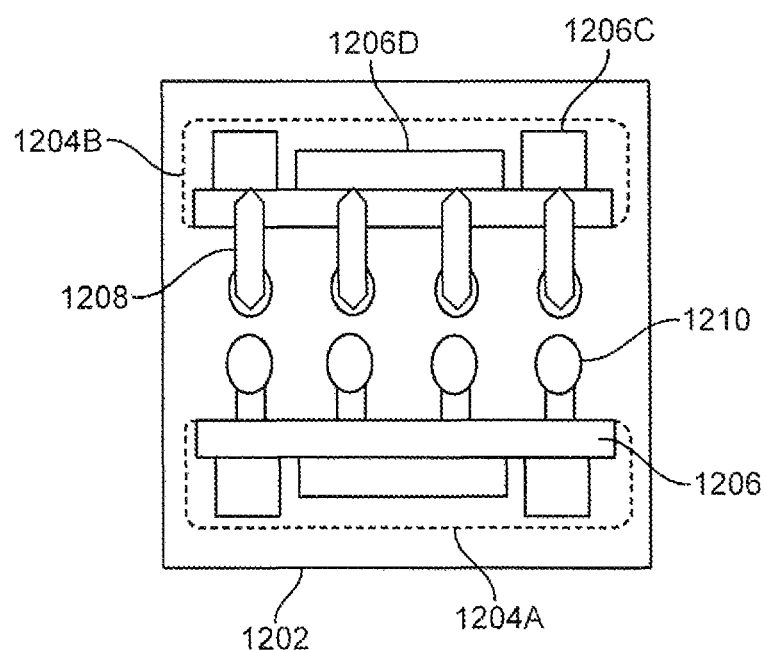
FIG. 12 is a side, partial sectional view of an optical assembly included in the distal portion of FIG. 6, in accordance with an embodiment.

FIG. 12 illustrates a cross-sectional view of the optical assemblies 610 of FIG. 6, in accordance with an embodiment. There may be two or more optical assemblies 610 on a distal portion 600 of a multimodal brain sensing lead according to embodiments, and the optical assemblies may be substantially identical in terms of the components used in the same or they may have different types of components or components with varying specifications (e.g., the wavelengths of the LEDs may differ from optical assembly to optical assembly). Each optical assembly 610 may consist of a cylindrical lens 1202 surrounding two optoelectronic packages, 1204A and 1204B (hereinafter, "optoelectronic packages 1204", unless otherwise noted), according to an embodiment. In one embodiment, the lens is about 1.5 mm long, with an outer diameter of about 1.25 mm and an inner diameter of about 0.5 mm, and made of a clear biocompatible epoxy. Additionally or alternatively, the optical assembly 610 may be coated with sapphire to provide a hermetic seal around the electronics.

The two optoelectronic packages 1204 desirably are arranged on the lead so that they are roughly parallel to each other and 180 degrees from each other around the distal shaft 602C of the electronics module 602, in accordance with an embodiment.

In one embodiment, each optoelectronic package is about 1.5 mm long, about 0.5 mm wide and about 0.3 mm thick. In yet another embodiment, each optoelectronic package contains two LEDs (an LED 1206C is labeled in FIG. 12), preferably an 805 nm LED and a 630 nm LED, and a photodetector (a photodetector 1206D is labeled in FIG. 12) sensitive to both LED wavelengths. For a given application of a multimodal brain sensing lead, the wavelengths of the LEDs may be selected for making effective blood volume and oxygenation measurements. The electronics are mounted onto a ceramic base 1206. Each optoelectronic package 1204A and 1204B shown in FIG. 12 is provided with four electrical contacts, including an electrical contact for the positive contact of each LED and the photodiode and for a common ground. The electrical contacts may be connected via 0.100 mm PtIr wires 1208 to electrical contacts 1210 on the distal shaft 602C. The optoelectronic packages 1204 preferably are made moisture-proof and are hermetically sealed by encasing them in a metal electronics package with a glass window above the optical elements and glass feedthroughs for the wires connecting to the distal shaft 602C of the electronics module 602. The lens epoxy insulates the wires connecting the optoelectronics module to the distal shaft 602C.

Figure 13:
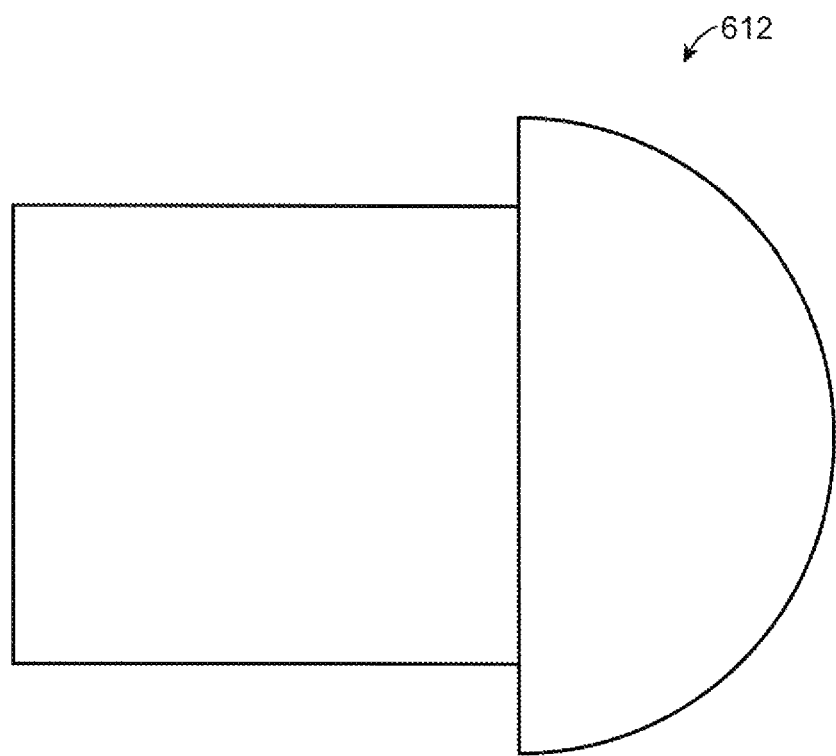
FIG. 13 is a side, enlarged view of the distal tip of FIG. 6, in accordance with an embodiment.

FIG. 13 is a view of a distal tip 612 (also shown in FIG. 6). In this embodiment, the distal tip 612 of the lead is cylindrical with a total length of about 1.625 mm and a rounded end. It is made of PEEK. The proximal 1 mm or so of the distal tip 612 has a diameter of about 0.9 mm, while the distal 0.625 mm or so of the distal tip 612 has a diameter of about 1.25 mm and is hemispherically shaped to facilitate blunt dissection and avoid puncturing blood vessels as it is inserted into the brain. The proximal 1 mm or so of the distal tip 612 may be press-fit into the most distal macroelectrode contact.

Multimodal Strip Brain Sensing Lead.

The foregoing discussion is directed primarily to a multimodal brain sensing lead the distal portion of which is intended to be used as a depth lead or deep brain lead, that is, the distal portion is intended to be implanted into neural tissue of a patient's brain. In a depth lead, components (such as transducers) used to acquire measurements for a given sensing modality may be oriented to best suit the in-brain implant location.

For example, a macroelectrode may comprise a ring electrode such that a conductive surface of the electrode is exposed to the tissue all around the circumference of the distal portion of the lead. An optical sensor may be configured so that an illuminating element, a light-receiving element and/or a lens is oriented in a particular direction relative to the distal shaft of the lead. A strip lead is designed to rest on a surface of the patient's brain rather than to be implanted into the brain tissue. Accordingly, a component of a sensing modality may be oriented differently than in a depth lead application, so as to best acquire the physiological data from the patient.

For example, whereas a macroelectrode may be in the form of a ring or cylindrical electrode on a depth lead, in a strip lead configuration, the macroelectrode may be in the form of a disk the conductive surface of which is designed to rest against a surface of the brain when the distal portion is implanted. Thus, the macroelectrode is provided in the strip lead so that it is configured to be receptive only to the region of brain tissue underneath it, and not to the opposite-facing surface (i.e., the surface of the macroelectrode facing out towards the skull).

The selective receptiveness of the macroelectrode may be accomplished using insulation. The multimodal strip lead may be configured to have each or all of the same sensing modalities as a multimodal depth brain sensing lead. It will be appreciated that one or more components of each sensing modality might be implemented differently, for example, in terms of conductive surfaces or orientation, to optimize the modality for the strip lead application.

Proximal Portion of Multimodal Strip Brain Sensing Lead

The proximal portion of a multimodal strip brain sensing lead may be configured in substantially the same way as the proximal portion of a multimodal depth brain sensing lead, for example, where the device which is acquiring the measurements from each sensing modality and to which each lead is to be connected are the same. ID the embodiments of a multimodal strip brain sensing lead described herein, for example, the proximal portion is identical to the to the proximal portion 100 of the multimodal depth brain sensing lead of FIG. 1.

Distal Portion of the Multimodal Strip Brain Sensing Lead

Figure 14:
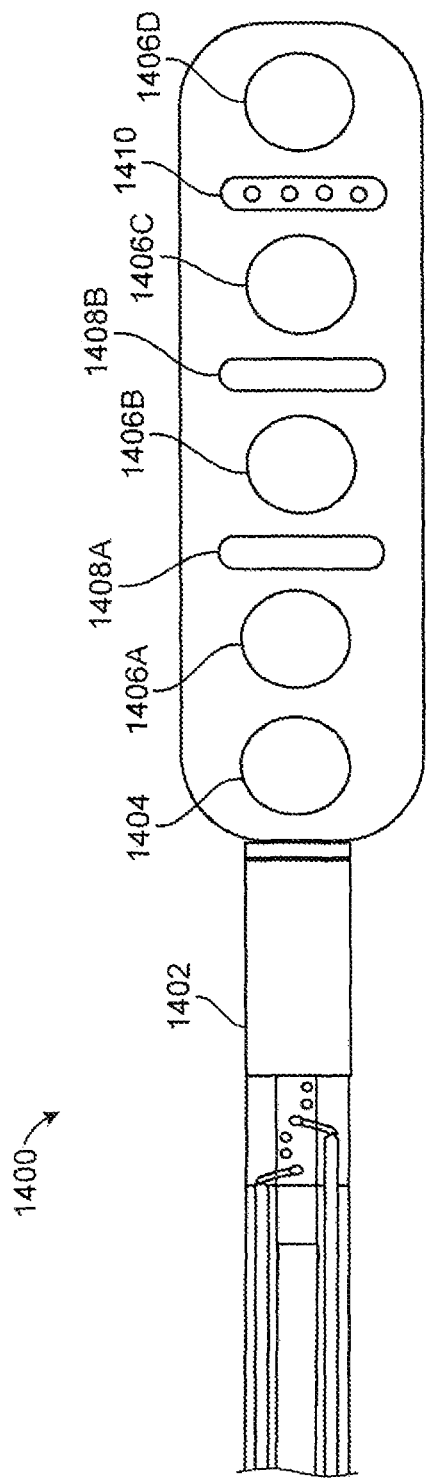
FIG. 14 is a bottom, partial sectional view of a distal portion of a multimodal strip sensing lead, in accordance with an embodiment.
Figure 15:
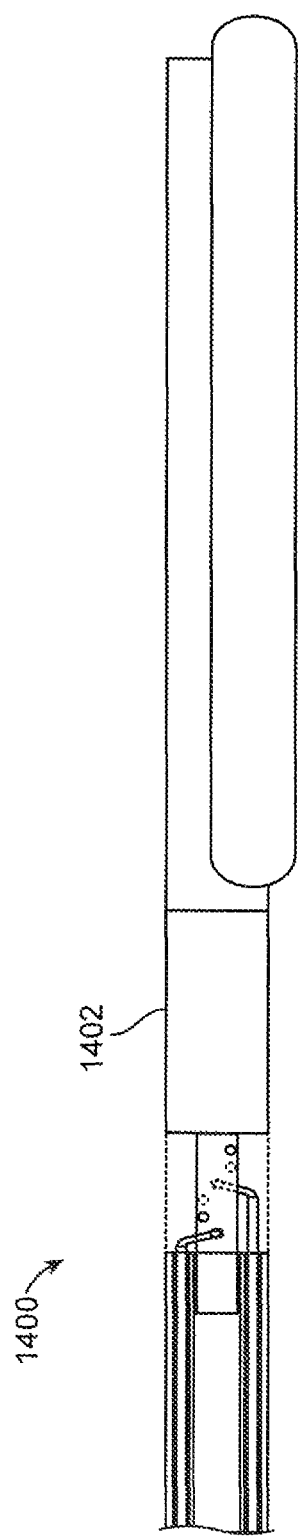
FIG. 15 is a side partial sectional view of the distal portion of FIG. 14.

FIG. 14 is a bottom view of a distal portion of a multimodal strip sensing lead, in accordance with an embodiment. FIG. 15 illustrates a side, partial sectional view of the distal portion 1400. The distal portion 1400 consists of a flattened piece of silicone containing a plurality of sensor components (e.g., transducers). More specifically, the distal portion 1400 includes an electronics module 1402, a voltammetry ground/reference 1404, macroelectrodes 1406A, 1406B, 1406C and 1406D, a first optical assembly 1408A and a second optical assembly 1408B, and a microelectrode assembly 1410. A distal shaft of the electronics module 1402 (shown in FIGS. 14 and 15) is similar to the distal shaft of the multimodal depth brain sensing lead described above, but in the strip lead, the electronics module 1402 is configured in a way that encourages the strip to remain flexible (e.g., floppy) and to lay approximately flat upon implantation.

Measurement Acquisition

In embodiments, acquiring a measurement from a plurality of sensing modalities may involve several steps. Before any measurements can be acquired, the sensor must be configured appropriately. For field potential measurements, single unit neuronal activity recording and neuronal multi unit activity recording, electrophysiological sensing, electrodes, amplifier gain and filter settings, and sampling rate must be selected. For the optical sensing modalities (i.e., optical blood volume and optical blood oxygenation measurements), LEDs, photodetectors, brightness, gain, integration time, and sampling rate must be selected. For the voltammetry modality, voltage waveforms and scan rates must be selected. For the rheoencephalography modality, electrodes, waveforms, and scan durations must be selected.

Once the sensing modalities (and associated components of each) have been initially configured, and then acquiring measurements from each modality may be accomplished in accordance with a timing schedule. When acquisition of a measurement is triggered pursuant to the timing schedule, the measurements are collected, digitized and stored in the host device.

Figure 20:
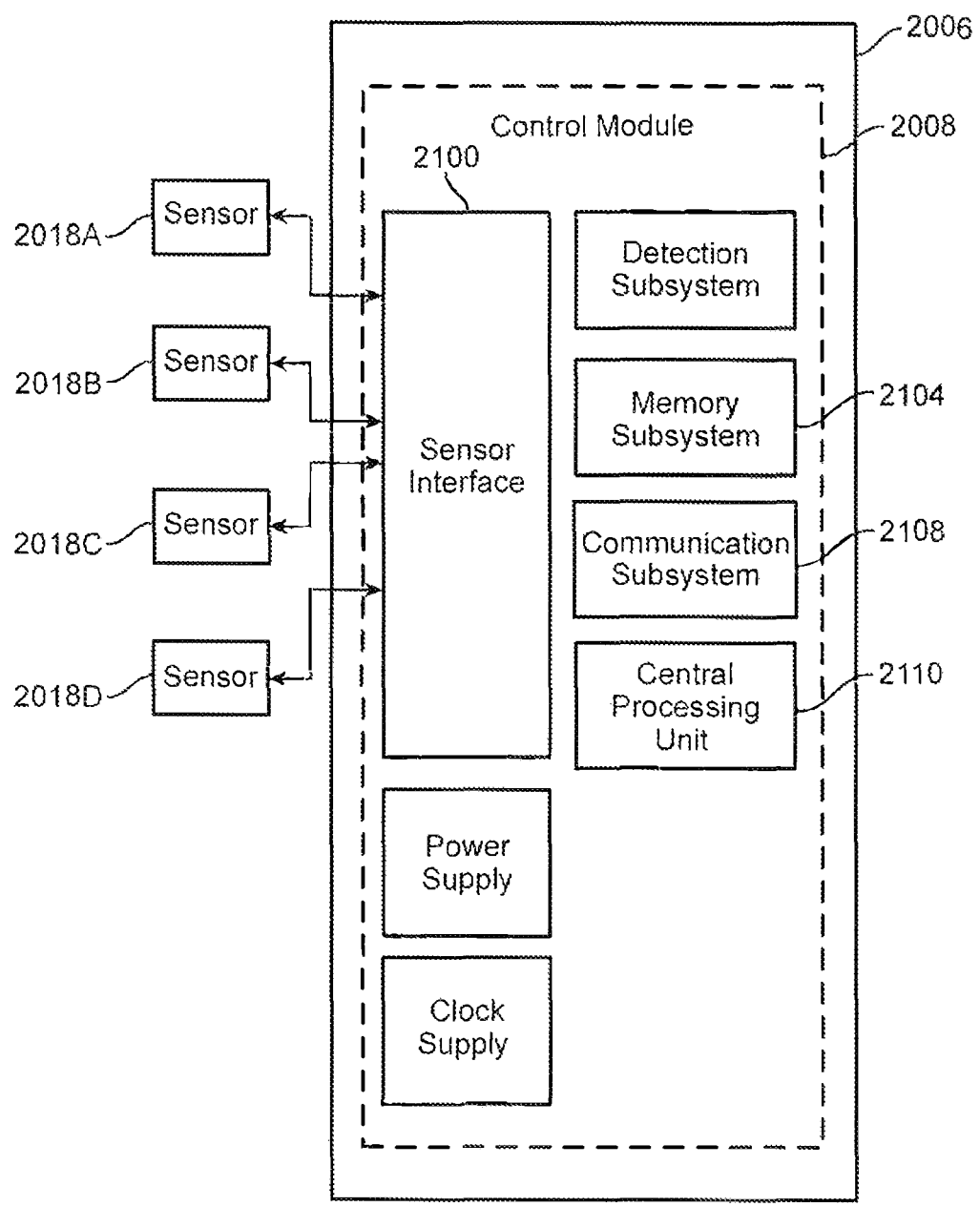
FIG. 20 is a block diagram illustrating the functional relationship of some of the implantable components of an implantable medical device system, with which embodiments of a multimodal brain sensing lead may be used.

Referring now to FIG. 20, a host device 2006 (e.g., an implanted medical device) may be configured to receive the data acquired from the sensing modalities of the multimodal brain sensing lead through a sensor interface 2100. (In FIG. 20, four sensors 2018A, 2018B, 2018C, and 2018D represent the one or more sensing modalities implemented in one or more instances of a multimodal brain sensing lead). The sensor interface 2100 may be configured to subject the acquired data to subsequent signal processing (e.g., amplification, filtering, and other smoothing of waveforms, etc.).

The data may also be operated on by one or more algorithms running in the host device, for example, in control module 2008 including a detection subsystem 2102 and controlled by a CPU 2110, such as a pattern or feature detection algorithm or a time-dependent detection algorithm or another algorithm that looks for certain predefined "events" or sequences of events in a measured signal, including but not limited to a state-detection algorithm. The output of a detection algorithm or algorithms can be used as part of a closed-loop system, for example, via a communications subsystem 2108, to trigger delivery of a therapy such as electrical stimulation. Examples of detection algorithms that may be used in connection with an implantable medical device receiving signals sensed from brain leads are described in, for example, U.S. Pat. No. 6,810,285 to Pless et al. for "Seizure Sensing and Detection Using an Implantable Device" issued Oct. 26, 2004 and U.S. Pat. No. 7,341,562 to Pless et al. for "Modulation and Analysis of Cerebral Perfusion in Epilepsy and Other Neurological Disorders" issued Mar. 11, 2008. Each of U.S. Pat. Nos. 6,810,285 and 7,341,562 are hereby incorporated by reference in the entirety.

A host device 2006 further may include a memory subsystem 2104 for recording and/or storing (permanently or temporarily) information obtained from the sensors or about a condition of the device (e.g., remaining battery life). The host device may include a power supply 2106, such as a primary cell or rechargeable battery, and a clock supply 2112 to provide timing signals for, e.g., acquiring measurements from the various sensing modalities implemented on a multimodal brain sensing lead.

Figure 17:
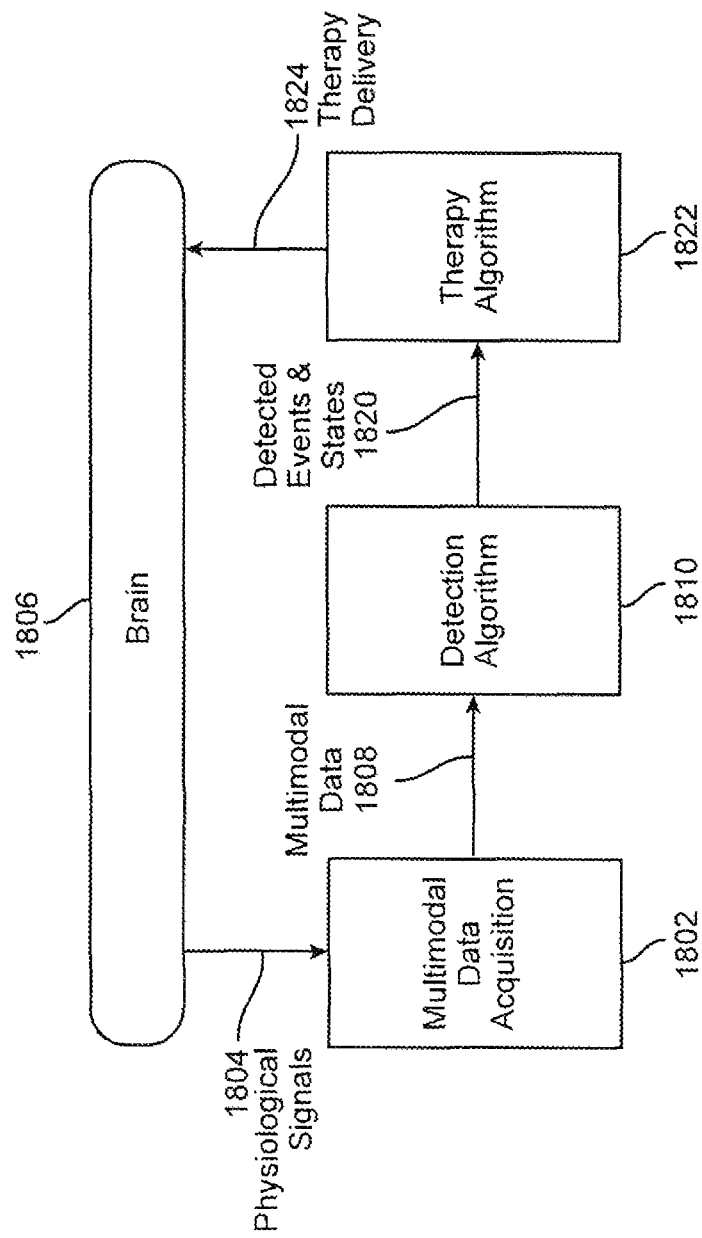
FIG. 17 is a schematic illustration of an example of how data obtained from a multimodal brain sensing lead might be used in a closed-loop therapy delivery system in accordance with embodiments.

FIG. 17 is a schematic diagram of one example of a closed-loop system with which a multimodal brain sensing lead according to embodiments may be beneficially used. Multimodal data acquisition 1802 based on physiological signals 1804 sensed from the patient's brain 1806 made possible by the multimodal brain sensing lead(s) are transmitted in the form of multimodal data 1808 to a detection algorithm or algorithms 1810 running in a host device (such as another implanted component of the implantable medical device system that includes the multimodal brain sensing lead(s)). Each detection algorithm 1810 runs according to parameter values that may be programmed in advance for the algorithm or calculated in real time. The output of a detection algorithm 1810 may be detected event(s) or state(s) 1820 which are provided as the input to one or more therapy algorithm(s) 1822. Each therapy algorithm 1822 may also run according to parameter values that may be preprogrammed or calculated in real time, depending on the particular application of the medical device system. A therapy algorithm 1822 may cause a therapy (e.g., in the form of a burst or bursts of pulsatile electrical stimulation or in the form of a bolus of a drug) to be delivered 1824 to the brain 1806 in response to the detection algorithm(s) 1810 and the multimodal data 1808 acquired from the multimodal brain sensing lead.

The host device may also have the capacity to store data acquired from the sensing modalities via the multimodal brain sensing lead, for example in one or more areas of memory 2104 in the host device 2006.

Figure 19:
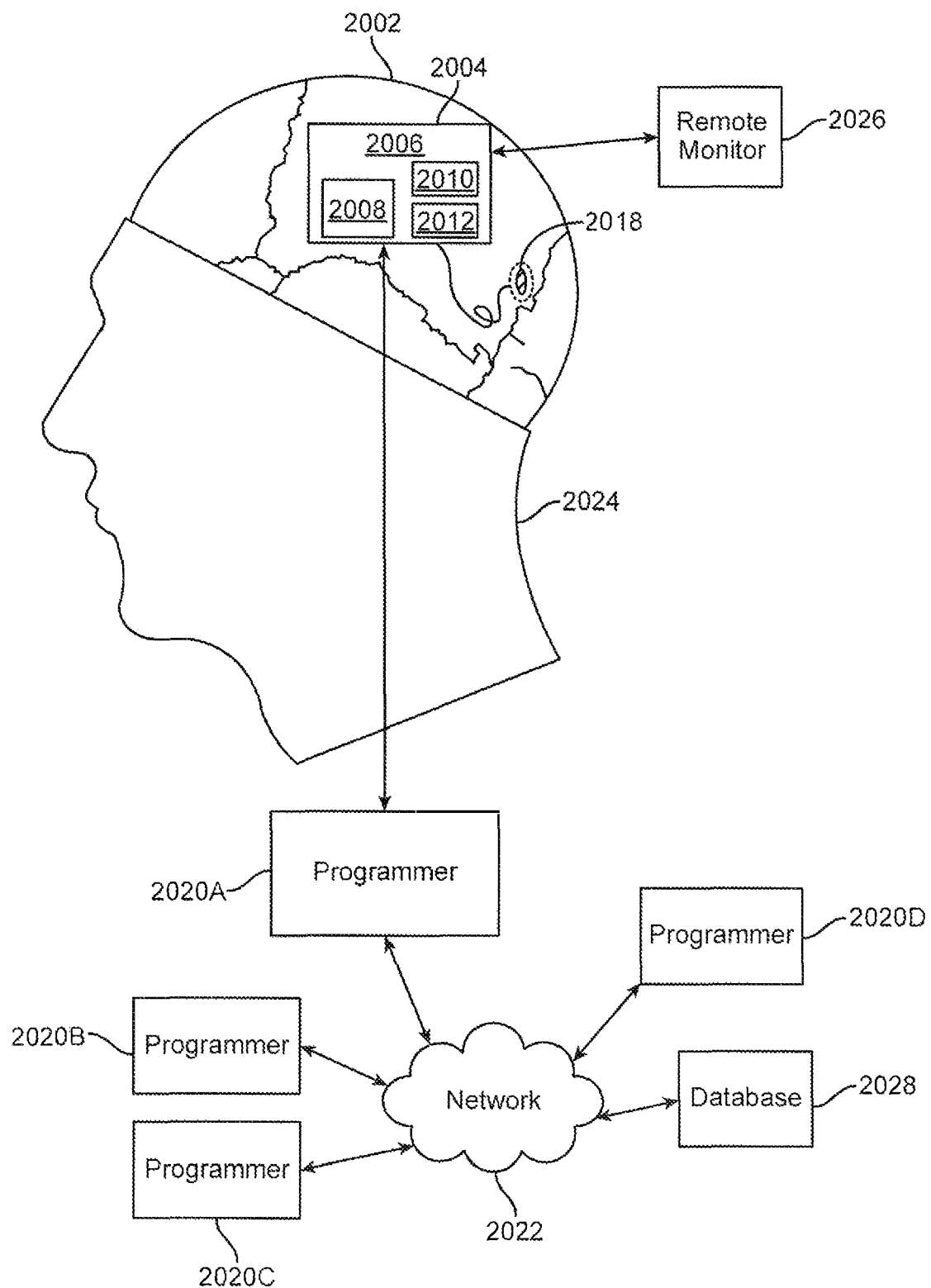
FIG. 19 is a schematic diagram of an example of an implantable medical device system with which a multimodal brain sensing lead according to embodiments may be used.

Referring now to FIG. 19, if the host device is, like the multimodal brain sensing lead, an implantable component of an implantable medical device system, the host device may be configured to communicate with one or more external components via a wireless communications link (such as a form of telemetry). The communication may be bidirectional, so that an external component (e.g., a physician's "programmer") can be used to program the host device and/or to initially configure each sensing modality prior to data acquisition from the patient (e.g., to set amplifier gains and sampling rates) and so that one or more types of external components (e.g., the physician's programmer and a patient "remote monitor") may be used to download data from the implanted host device and subsequently store it on the external component. In FIG. 19, represented schematically are four physician programmers, namely, programmers 2020A, 2020B, 2020C, and 2020l) and a patient remote monitor 2026.

In some implantable medical device systems, the external components may be configured to interface with one or more networks (a network 2022 is shown in FIG. 19) and/or a centralized database which is used for storing data acquired from the sensing modalities and/or initial settings for each sensing modality (a database 2028 is shown in FIG. 19). Data may be transmitted from an external component through a telephone or broad band connection to a central database. Communication with a database may also be accomplished over the internet via a secure website.

A display provided on an external component such as a programmer or a website may be used by a patient's physician or other caregiver to review and manipulate data acquired from each sensing modality. For example, a programmer or website may be used by a physician to look at data acquired from each of a plurality of sensing modalities from a given patient at or about the same time.

Figure 16:
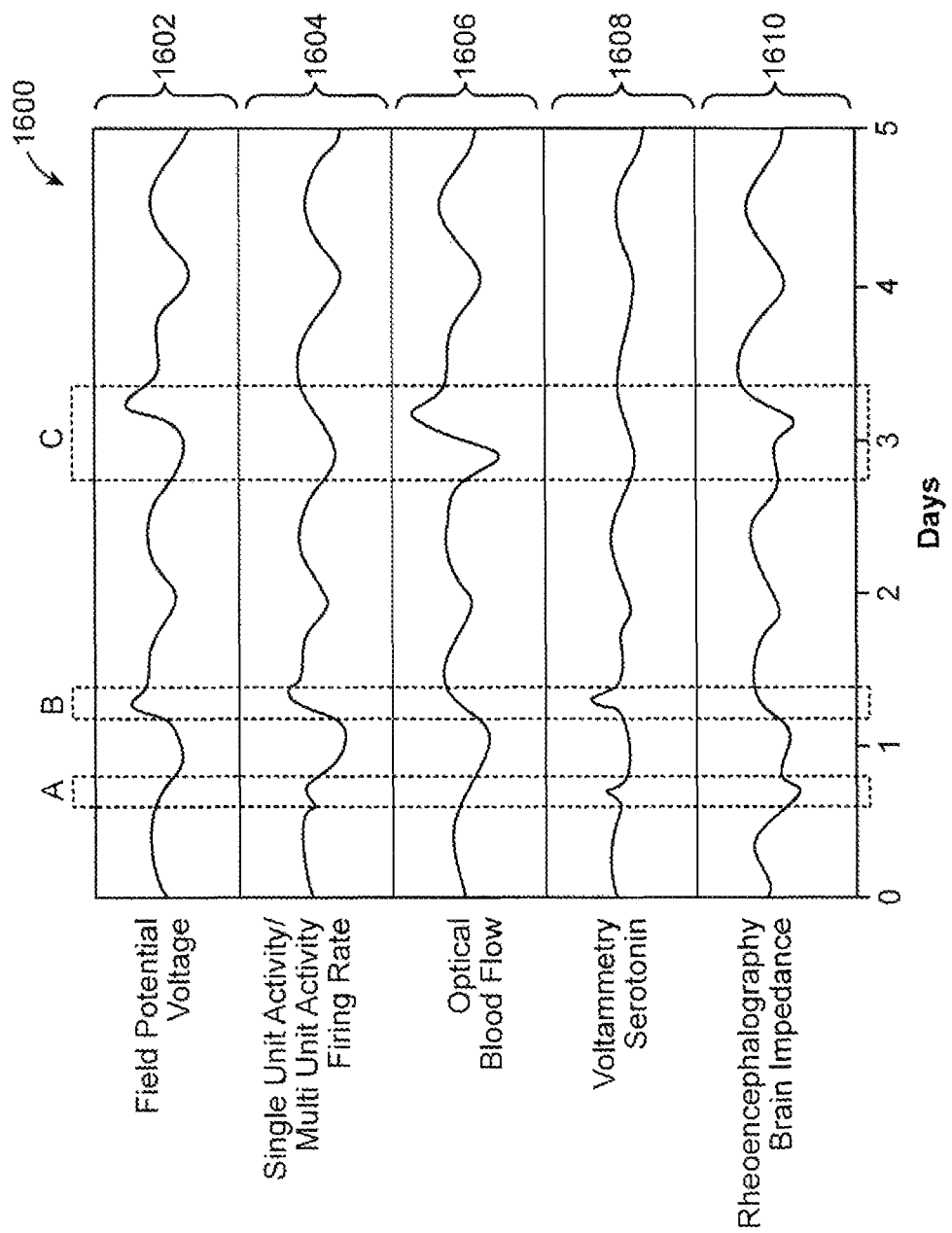
FIG. 16 is a series of graphs representing the type of information that might be obtained over time from each of five different sensing modalities and then displayed to a user in accordance with embodiment.

FIG. 16 is an example of a display that might be provided to a user on a programmer or over a secure website corresponding to data acquired from different sensing modalities of a multimodal brain sensing lead according to embodiments over time. More particularly, FIG. 16 is a display with a series of five graphs 1602, 1604, 1606, 1608, and 1610. Each graph corresponds to a single period of data acquisition in days. The first graph 1602 corresponds to a field potential measurement acquired using a field potential measurement modality implemented with components on a multimodal brain sensing lead; the second graph 1604 corresponds to a single unit activity/multi unit activity measurement acquired using either a single unit activity measurement or a multi unit activity modality implemented with components on the same multimodal brain sensing lead; the third graph 1606 corresponds to an optical blood flow measurement acquired using an optical measurement modality (e.g., optical blood volume measurement modality or optical blood oxygenation measurement modality) implemented with components on the same multimodal brain sensing lead; the fourth graph 1608 corresponds to voltammetry measurement (of serotonin concentration) acquired using a voltammetry measurement modality implemented with components on the same multimodal brain sensing lead; and the fifth graph 1610 corresponds to a rheoencephalography measurement acquired using a rheoencephalography modality implemented with components on the same multimodal brain sensing lead.

The ability to visualize data acquired from different sensing modalities from a common location in the patient's brain at or about the same time will be clinically useful for evaluating such things as the status of a patient, the patient's response to a therapy, such as a therapy that might be delivered by a host device or another implantable component of an implantable medical device system that includes the multimodal brain sensing lead, or other therapies the patient may be receiving.

Electrophysiological Recording Example

In this example, a multimodal brain sensing lead is surgically implanted with its distal end oriented towards or in a hippocampal region of a human patient. The hippocampus is selected because the patient has epilepsy with seizures originating in the hippocampus, and abnormal electrographic activity, including electrographic seizures and interictal discharges, is expected to be observed in the hippocampus. Neuronal field potential, neuronal single unit activity, and neuronal multi unit activity measurement acquisition is configured with the objective of recording neuronal activity for diagnostic and therapeutic purposes. Diagnostic use includes recording and storing measurements of neuronal activity for later review by a clinician. Therapeutic use includes automatic analysis of neuronal activity measurements by computational algorithms in the host device, and subsequent therapy delivery. This analysis is performed in a closed-loop manner to determine when therapy, for example, electrical stimulation, should be delivered. Thus far, this scenario is similar to that used for neuronal field potential recording by the responsive neurostimulation systems under investigation by NeuroPace, referred to as the "RNS SYSTEM". Field potential recording from implanted electrodes also is described in U.S. Pat. No. 6,016,449 to Fischell et al. for "System for Treatment of Neurological Disorders" issued Jan. 18, 2000, as well as in U.S. Pat. No. 6,810,285. Both of U.S. Pat. Nos. 6,016,449 and 6,810,285 are incorporated by reference in the entirety herein.

Field Potential Measurement Acquisition

In an embodiment, a field potential recording is configured by adjusting the settings for field potential amplification and analog-to-digital conversion in a host device, such as an implanted responsive neurostimulator configured for acquiring measurements from two or more of the different sensing modalities of the multimodal brain sensing lead. This initial configuration is performed by a clinician using software implementable on an external device such as a general purpose computer (e.g., laptop or handheld computer), which is designated a "programmer". Software miming on the programmer is specifically designed to provide the user with a graphical user interface to communicate with and configure the host device and one or more multimodal brain sensing leads (e.g., a depth lead and a strip lead, or two depth leads, or two strip leads) or some other combination of three or more multimodal brain sensing leads).

In this example, the system is configured so that field potential measurements are acquired on two channels of the host device. The first field potential measurement channel will be used to sense things such as field potential spikes, waves and oscillatory activity from neurons near a pair of macroelectrodes on the multimodal brain sensing lead. This channel is configured for differential recording. First, one of two amplifiers in the host device is selected for field potential recording: for the purposes of this example, the selected amplifier will be designated the first amplifier and the other of the two amplifiers will be designated the second amplifier. Next, input sources for the amplifier in order to acquire the differential measurement are selected: in this example, the input sources comprise three macroelectrodes located on the distal portion of a multimodal brain sensing lead and a conductive housing provided for the host device (e.g., the housing of an implanted responsive neurostimulator). For one differential measurement, a pair of adjacent macroelectrodes is selected as input sources. More specifically, a first macroelectrode is selected as the input and a second macroelectrode as the reference for the first field potential amplifier. These electrodes are selected because they are adjacent to each other on the lead and field potential information from the neurons in the vicinity of the first and second macroelectrodes is desired. Selection of a pair of electrodes is commonly used for differential recording. Differential mode is selected because a field potential signal describing differences between neural activities at two macroelectrodes is desired. This signal will reflect primarily activity near the electrodes and subtract out background activity common to both electrodes.

Next, filter settings are selected. For the purposes of this example, it is assumed that the first channel will be used primarily for recording in the standard delta to gamma EEG frequency range, approximately 3 to 100 Hz. Accordingly, a high-pass filter associated with the channel may be set at 1 Hz, and a low-pass filter at 100 Hz. These settings are typical for field potential recording. A notch filter is not enabled in this particular circumstance because power line noise is not expected to be a problem. A notch filter may be enabled later if noise is encountered.

Next, a gain setting is selected. For the purposes of this example, for the first channel, a gain of 100 is selected because field potential voltage spikes of approximately ±10 mV are expected. This will result in approximately ±1 V output from the amplifier. This is within the amplifier's dynamic range, assuming the amplifier is powered with 3.5 V, which is typical of implanted devices.

Finally, a sampling rate is selected. This is the rate at which the analog-to-digital converter converts voltage measurements to digital values. A sampling rate of 250 samples per second is selected. This sampling rate is sufficient for EEG field potential recording in the 3-100 Hz range.

The second field potential measurement channel will be used for single ended DC recording (as distinguishable from a differential recording mode). Particularly in an application where a multimodal brain sensing lead is used to acquire localized information from a patient with epilepsy, single ended DC recording is desirable because DC voltage changes may be associated with seizures and seizure onsets and are not detectable with differential recording. First, an amplifier, input and reference are selected for field potential recording. The clinician selects the second field potential measurement amplifier in the host device with the third macroelectrode selected as an input, and the conductive housing of the host device, which serves as a patient ground, selected as a reference. Using a macroelectrode on the distal portion of an implanted lead and patient ground as the amplifier inputs is common for single ended DC recording. The third macroelectrode is selected as the input because low frequency voltage change information is desired from the brain area in the vicinity of the electrode. The host device housing is selected as the reference because its large surface area makes it a good source for patient ground.

Next, filter settings are selected. The second field potential measurement channel will be used for recording DC and very low frequency. Thus, for the purposes of this example, a high-pass filter is set at either DC (no filter) or the lowest available frequency setting (which may be about 0.01 Hz). DC (no filter) is selected if a constant measurement of DC offset is desired, while a low frequency filter setting is selected if only measurement of transient DC shifts is desired. A low-pass filter is set at the lowest available setting (which may be about 10 Hz). This setting of the low pass filter generally will be satisfactory for low frequency field potential recording in the range of 0-10 Hz. Again, in this example, a notch filter is not enabled because power line noise is not expected to be a problem. A notch filter may be enabled later if noise is encountered.

Next, a gain setting is selected. For this second field potential measurement channel, a gain of 10 is selected because the DC baseline shifts associated with seizure onsets and changes in cerebral blood flow are expected to be relatively large. A gain of 10 will keep the ±175 mV field potential EEG changes within the dynamic range of the amplifier, assuming a 3.5 V power supply.

Finally, a sampling rate is selected. A sampling rate of 10 samples per second is selected because field potential EEG baseline voltage changes are expected to be relatively slow, and because this slow sampling rate will allow power to be conserved by using a low duty cycle for the amplifier and analog-to-digital converter.

After the first and second amplifiers for each of the two field potential measurement channels are initially configured by the user, measurement acquisition may be performed automatically according to a data acquisition timing schedule. Alternatively, measurement acquisition may be initiated manually by the user.

When a field potential measurement is acquired, each field potential measurement amplifier and its associated analog-to-digital converter (ADC) are powered on. The amplifier is allowed to warm up and stabilize for a few milliseconds, and then the signal is digitized at the sampling rate that was selected by the user when the field potential measurement amplifiers were initially configured. Digitized field potential measurement voltage values are then stored in memory for subsequent analysis and transmission outside the host device into an external database. In an embodiment, for field potential recording, each of the amplification, analog-to-digital conversion, and data storage occur within the host device.

Neuronal Single Unit Activity (SUA) and Neuronal Multi Unit Activity (MUA) Measurement Acquisition In an embodiment, either of the modalities for neuronal single unit activity measurement and neuronal multi unit activity measurement can be configured by adjusting the settings for amplification and analog-to-digital conversion in the multimodal brain sensing lead using software in an external component (such as a programmer). A single amplifier channel can be configured for combined single unit activity measurements and multi unit activity measurements. A differential amplifier in the electronics module of the lead is used for single unit activity and multi unit activity sensing. Electronics in the lead likely will be needed for single unit activity and multi unit activity recording (measurement) because there is no direct wire connection between individual microelectrodes and the proximal portion of the multimodal brain sensing lead. There is also one macroelectrode used for voltammetry and single unit activity and multi unit activity recording that is only connected to the electronics module. Because of this, single unit activity and multi unit activity electrodes are connected to an amplifier in the electronics module, the amplifier output is digitized by an analog-to-digital converter in the electronics module, and the digitized output signal is transmitted to the host device which is connected to the proximal portion of the lead. Subsequent signal processing and data storage then can be accomplished in the host device.

In this example, two channels are configured for use in recording (measuring) either single unit activity or multi unit activity (or both at the same time) from the patient. The first single unit activity/multi unit activity channel is configured for differential recording. This first channel will be used to look for differential single unit activity (or multi unit activity as the case may be) such as in the form of spike waveforms from single neurons (or local populations made up of multiple neurons). First, one of two amplifiers in the electronics module of the distal portion of the multimodal brain sensing lead is selected for single unit activity recording (or multi unit activity recording): for the purposes of this example, the selected amplifier will be designated the first amplifier and the other of the two amplifiers will be designated the second amplifier for single unit activity/multi unit activity recording.

Next, input sources are selected for the amplifier. A pair of electrodes is selected as input sources. A first microelectrode is selected as the input and a second microelectrode is selected as a reference for the first single unit activity/multi unit activity amplifier. These first and second microelectrodes are selected because they are adjacent to each other on the multimodal brain sensing lead and single unit activity/ multi unit activity information from the neurons in the vicinity of the first and second microelectrodes is desired. Selection of a pair of electrodes is commonly used for differential recording. Differential mode is selected because a signal describing differences between neural activities at two microelectrodes is desired. This signal will reflect primarily activity near the electrodes and subtract out background activity common to both microelectrodes.

Next, filter settings are selected. This channel will be used primarily for recording extracellular neuronal action potential waveforms, which have high frequency content, approximately 100-5000 Hz. A high-pass filter is set at 100 Hz, and the low-pass filter is set at 5000 Hz. These settings are typical for single unit activity and multi unit activity recording. The notch filter is not enabled because power line noise is not expected to be a problem. It may be enabled later if noise is encountered. Next, a gain setting is selected. For this channel, a gain of 100 is selected because the single unit activity and multi unit activity voltage spikes of approximately ±10 mV are expected. This will result in approximately ±1 V output from the amplifier. This is within the amplifier's dynamic range, assuming the amplifier is powered with 3.5 V, which is typical of implanted devices.

Finally, a sampling rate is selected. This is the rate at which the analog to digital converter converts voltage measurements to digital values. A sampling rate of 5000 samples per second is selected. This sampling rate is sufficient for single unit activity and multi unit activity recording in the 3-100 Hz range.

Continuing with the example, a second single unit activity/multi unit activity channel will be used for single ended recording between a microelectrode and fifth macroelectrode which is connected to the electronics module of the multimodal brain sensing lead. This channel is configured identically to the first single unit activity/multi unit activity channel, with the exception of electrode inputs to the amplifier, which are a third microelectrode and the aforementioned fifth macroelectrode. The macroelectrode provides a relatively stable background reference voltage that is subtracted from the microelectrode signal, resulting in measurements that mainly reflect single unit activity (or multi unit activity as the case may be) at the microelectrode.

Optical Measurement Acquisition

In an embodiment, optical blood volume measurements and optical blood oxygenation measurements are acquired using the multimodal brain sensing lead for such purposes as estimating blood flow, blood oxygenation, blood pressure, heart rate, and breathing rate. When a measurement is made, a light emitting diode (LED) is illuminated and a photodiode (PD) is used to measure light reflected from the illuminated tissue. The photodiode output is amplified, digitized, and transmitted to the host device. Several parameters are configured based on empirical testing in order to optimize clinical utility. These include the following: selection of the LED and photodiode; LED brightness; photodiode amplification; and analog-to-digital converter sampling rate. The LED and photodiode are selected to ensure that the signal comes from the tissue of interest and any artifacts are minimized.

For some measurements, such as blood oxygenation measurements, two LEDs each with different wavelengths may be illuminated alternately. LED brightness is adjusted to maximize signal to noise, make optimal use of the photodiode's dynamic range, and minimize power consumption Amplification of the photodiode output may require a long integration time, which will limit the sampling rates available. Integration time and sampling rate are selected based on the physiological parameter being measured. For example, blood flow and blood oxygenation change slowly, so a low brightness, low sampling rate (e.g., 1 Hz) and a long integration time (e.g., 1 second) may be used. Heart rate is much faster and thus many samples per cardiac cycle (e.g., 10-100 samples per second) may be required to reconstruct a cardiac waveform. Blood pressure and breathing rate may also be determined by evaluation of cardiac waveform data.

Even though multiple physiological variables are measured by optical sensing, the basic measurement process is the same for each variable. An individual measurement is made in the following manner First, based on a pre-determined timing schedule, a host device instructs the electronics module of the multimodal brain sensing lead to illuminate a specific LED at a specific intensity. Next, the host device sends a signal to an amplifier in the electronics module to connect to a specific photodiode in the lead. Finally, the host device instructs the amplifier and the analog-to-digital converter in the multimodal brain sensing lead to amplify and digitize the light received by the photodiode for a selected integration time. After the integration period, the LED is powered down and illumination is stopped. The digitized light level is then sent from the electronics module to the host device for signal processing. This process is repeated for each measurement.

Multiple physiological variables can be measured at the same time by interleaving the acquisition of multiple optical signals. Measurements for individual physiological variables can then be derived from the multiple signals.

Multiple optical signals are acquired using several different combinations of LEDs and photodiodes. This is done by collecting data from each photodiode in combination with each LED and comparing the signals.

In an example, a multimodal brain sensing lead is provided with four optical assemblies, namely, a first, a second, a third, and a fourth optical assembly. The first and second optical assemblies are provided on the lead more distally than are the third and fourth optical assemblies. The first optical assembly is provided so that it is back-to-back with the second optical assembly (i.e., so that the first optical assembly is pointed about 180 degrees away from the second optical assembly relative to the circumference of the depth lead). The third optical assembly is also provided so that it is back-to-back with the fourth optical assembly. The first and third optical assemblies are oriented on the lead so that they point in the same direction. The second and fourth optical assemblies are oriented on the lead so that they point in the same direction, which may be a different direction than the direction in which the first and third optical assemblies point. Each of the four optical assemblies is provided with a photodiode and two LEDs, each LED characterized with a different wavelength. In one example, the wavelengths for the two LEDs in each of the optical assemblies are 805 ran and 630 nm.

For data acquisition from the first optical assembly, data samples are acquired using the photodiode in combination with the two LEDs of different wavelengths. The two LEDs are used together so that tissue oxygenation measurements based on the ratio of the two wavelengths may be calculated. The two LEDs are alternately illuminated at moderate illumination intensity for duration of 16 ms each, or 31.25 samples per second for each wavelength for 15 seconds. Then the same timing pattern is used to collect samples using the second optical assembly, followed by the third optical assembly, followed by the fourth optical assembly. The cycle is repeated every minute. These results in eight signals corresponding to light emitted from each of the LEDs in each of the four optical assemblies. Each signal consists of a repeating pattern of 15 seconds of data samples followed by a 45-second pause. FIG. 18 is an example of the sort of repeating pattern that might be used to acquire data from a set of four optical assemblies implemented in a multimodal brain sensing lead and processed by a host device, according to an embodiment. Each column in FIG. 18 represents one second. Each row in FIG. 18 indicates which photodiodes and LEDs of which of the four optical assemblies are active during that second. The pattern repeats continuously until stopped by the host device.

Optical data samples may be transmitted to the host device where they may be stored in data files on the host storage medium, which may be RAM memory or a hard drive.

The host device also may be configured to derive time series measurements of heart rate, respiratory rate, blood pressure, blood oxygenation and blood flow from the optical data samples using various algorithms Examples of these algorithms include the following.

Heart rate may be derived from any of the eight signals by identifying peaks in the signal and calculating the interval between peaks in minutes. The reciprocal of this is the heart rate in beats per minute.

Breathing causes a low frequency modulation of the optical cardiac waveform. Respiratory rate may be derived from any of the eight signals by filtering out the heart rate signal, finding the respiratory peaks in the filtered signal, and calculating the interval between peaks in minutes. The reciprocal of this is the respiratory rate in breaths per minute.

Blood pressure may be derived from any of the eight signals by measuring the difference between the optical cardiac waveform maximum during a cardiac cycle and the previous minimum. This difference is proportional to blood pressure and may be converted to blood pressure using previously collected calibration values. Alternatively or additionally, the systolic and diastolic blood pressures can be estimated from the systolic upstroke time and diastolic time in the optical cardiac waveform after application of calibration values.

Blood oxygenation may be derived from any pair of interleaved signals from the two LEDs of a given optical assembly on a multimodal brain sensing lead by calculating the ratio of these two signals and applying previously collected calibration values.

Blood flow and blood volume may be derived from any of the eight signals by calculating the average light intensity over several cardiac cycles. This value is proportional to the volume of blood in the illuminated tissue.

Voltammetry Measurement Acquisition

In an embodiment, voltammetry measurements are acquired using the multimodal lead for the purpose of estimating the concentration of oxidizable and reducible chemicals in the brain such as drugs (L-DOPA), neurotransmitters (dopamine, serotonin, glutamate, GABA), and other chemicals (hydrogen, oxygen). An example for clinical depression is the depression-related neurotransmitter serotonin and the drug fluoxetine Prozac). An example for movement disorders is the Parkinson's disease related neurotransmitter dopamine and the drug levodopa (e.g. Sinemet).

Voltammetry measurements may be acquired from the multimodal brain sensing lead by measuring the amount of current required (compliance current) to apply specific voltages to a microelectrode. The compliance current is proportional to the amount of material that is oxidized or reduced at the microelectrode.

Voltage may be varied using any of the methods commonly used for in vivo voltammetry. These include cyclic voltammetry and pulse voltammetry methods. An example of a fast scan cyclic voltammetry method uses a voltage sweep from −0.4 V to +1.2 V and back to −0.4 V is applied in a stepwise manner over a period of 9 milliseconds. Ten sweeps per second are made.

Pulse voltammetry methods are similar, but involve brief pulses at specific voltages, intended to measure molecules with specific oxidation and reduction potentials.

Compliance currents are digitized by an analog-to-digital converter and measurements are transmitted to the host device from the electronics module of the multimodal brain sensing lead. A number of measurement trials may be averaged, either in the electronics module of the multimodal brain sensing lead or in a host device to which the data from the voltammetry sensor(s) on the lead is transmitted. A background waveform may be similarly generated and then subtracted from the signal of interest Timing is determined by an acquisition timing schedule, which is described later.

Rheoencephalography (REG) Measurement Acquisition

In an embodiment, rheoencephalography measurements are acquired using an embodiment of a multimodal brain sensing lead provided with four macroelectrodes for the purpose of estimating brain tissue impedance which varies with blood flow and neural activity. Rheoencephalography measurements are acquired by transmitting a low current waveform between one of two pairs of macroelectrodes, where the macroelectrodes are a first, second, third and fourth macroelectrode. More specifically, in this example, the low current waveform is transmitted between the pair of macroelectrodes comprising the first macroelectrode and the second macroelectrode. The voltage of the waveform is measured between the pair of macroelectrodes comprising the third macroelectrode and the fourth macroelectrode. The third/fourth macroelectrode pair is positioned between the first/second macroelectrode pair, and along the same line as the first/second macroelectrode pair.

The transmitted waveform may be a continuous sine wave or an intermittent pulsed square wave. The frequency of the waveform may be adjusted in order to preferentially measure the impedance of different densities of tissue (e.g., blood) or specific compartments (e.g., extracellular space). The four macroelectrodes may be directly connected to a host device to acquire rheoencephalographic measurements. In this case, the host device beneficially can be used to generate the waveforms and measure the voltages with circuitry in the host device. The timing of the rheoencephalographic measurements may be determined by an acquisition timing schedule, which is described more fully below.

Measurement Acquisition Timing

In an embodiment, acquiring measurements from at least two different measurement modalities implemented in a multimodal brain sensing lead according to embodiments is accomplished according to a timing schedule. This schedule can vary considerably depending on which modalities are being acquired, and depending on Whether an electrical stimulation therapy or therapies' is also being delivered to the patient at or around the same time the measurements are being acquired (especially where one or more macroelectrodes of the multimodal brain sensing lead are being used for the dual purposes of sensing physiological data from the patient and delivering stimulation to the patient).

Modality-Specific Timing Considerations

In an embodiment, the timing of raw data acquisition depends on many factors. Among these are two considerations: (1) from which modalities measurements are desired;

and (2) what is the appropriate sampling rate for each modality. Sampling rates that might be appropriate for each modality are discussed below.

Acquiring Neuronal Field Potential Measurements

In an embodiment, choosing an appropriate sampling rate for the neuronal field potential measurement modality depends on the frequency range of interest. For example, and in general, there are two clinically relevant frequency ranges for neuronal field potential signals. The first is between DC and approximately 125 Hz. This is the range of standard EEG recording and covers delta, theta, beta, alpha, and gamma frequency ranges that are commonly used in clinical practice. A sampling rate of 250 samples per second is sufficient to capture neuronal activity in this range. The second range covers the high gamma frequencies, typically 125 to 500 Hz. A sampling rate of 1000 samples per second is sufficient to capture neuronal activity in this range. For both frequency ranges, higher sampling rates are more desirable, but recording (measuring) field potentials at the higher sampling rates generally require more power and computational resources (e.g., from a host device such as another implantable component of an implantable medical device system that includes a multimodal brain sensing lead).

Acquiring Neuronal Single Unit Activity and Neuronal Multi Unit Activity Measurements Action potentials of neurons typically have duration of 1-5 milliseconds. When an objective of the measurement is to acquire information about neuronal action potentials that would be suitable for the detection of spikes when they occur in a monitored signal and the subsequent classification of the spikes (e.g., sorting spikes into groups that have similar shapes and thus appear to have come from the same neuron, allowing quantification of action potential rate for each distinguishable neuron in the signal), then acquiring five to ten samples per action potential would probably be sufficient, however more are also acceptable. An appropriate sampling rate for recording action potentials in either the neuronal single unit activity measurement modality or the neuronal multi unit activity modality may be 5-10 thousand samples per second.

Acquiring Optical Measurements

Sensing modalities comprising information acquired using optical components include the optical blood volume measurement modality and the optical oxygenation measurement modality. In some embodiments, two physiological hemodynamic variables are measured using optical methods: heart rate; and blood oxygenation. Typical heart rates are below 180 beats per minute or 3 beats per second. In some embodiments, in order to acquire a meaningful measurement, for example, one that will describe a cardiac cycle, five to ten samples per heartbeat may be sufficient, but more may be acceptable. An appropriate sampling rate for measuring heart rate may be 15-30 samples per second. Blood flow and oxygenation changes may occur within 1-2 seconds, but more often changes may occur over tens of seconds to minutes. An appropriate sampling rate for blood flow and oxygen changes may be one to two samples per second.

Acquiring Voltammetry Measurements

Fast scan voltammetry measurements are made by scanning through a range of voltages. The scan duration depends on the voltage range and rate of change used, but a typical scan duration may be approximately 10 milliseconds. In between scans, there usually is a variable length inter-scan interval, which can also be expressed as a scan-to-scan interval, the reciprocal of which is the scan rate. For example, a 100 millisecond scan-to-scan interval is 10 scans per second. Within each scan, a sampling rate of 50-100 thousand samples per second may be used; if so, this would result in 500-1000 samples per 10 millisecond scan. The voltage scan waveform itself typically is generated at a much higher rate of 1 million samples per second using a voltage rate of 400 volts per second. Alternatives to fast scan voltammetry measurements that may also be used with the multimodal brain sensing lead according to embodiments include pulse voltammetry measurement methods, such as: (1) sampled current polarography; (2) normal pulse voltammetry; (3) differential pulse voltammetry; and (4) square wave voltammetry.

Acquiring Rheoencephalography Measurements

Rheoencephalography may be performed using either a continuous sine wave or intermittent square pulses. For sine wave rheoencephalography, a low amplitude forcing waveform in the range of 10-200 kHz is passed between one pair of electrodes and measured using a second pair of electrodes. A sampling rate of at least 10 times the forcing waveform frequency typically must be used. For square pulse rheoencephalography, the forcing waveform is a square pulse with a short duration, for example 1 millisecond, and a pulse-to-pulse interval is selected according to the expected physiological rate of change, for example 1 Hz. A much lower sampling rate equal to the forcing waveform pulse frequency may be used for square pulse rheoencephalography.

Measurement Acquisition Timing Examples

Continuous Acquisition with Multiple Modalities

Referring to Table 1, an example will be described in which a multimodal brain sensing lead is assumed to be configured to enable measurements in all of the sensing modalities discussed previously herein and in which measurements from all of the sensing modalities are acquired continuously with multiplexed timing. As for the field potential measurement modality, in this example the acquisition of neuronal field potentials is suspended during acquisition of rheoencephalographic measurements, and the acquisition of neuronal single unit activity measurements (or neuronal multi unit activity measurements, as the case may be) is suspended during acquisition of voltammetry measurements.

TABLE 1

| Modality | Sampling Rate | Notes |
|---|---|---|
| Field Potential Measurement | 250 samples/second | Suspended 1 sec during rheoencephalography |
| Single Unit and Multi unit activity Measurement | 5000 samples/second | Suspended 1 sec during voltammetry |
| Optical Blood Volume and Optical Blood Oxygenation Measurement | 20 samples/second | |

With reference to FIG. 21A, Table 2 illustrates the timing of measurement acquisition for the various sensing modalities over one minute. In Table 2, "FP" is "field, potential," "SUA/MUA" is "single unit activity/multi unit activity"; and "REG" is rheoencephalography. The dotted background in the first three rows of Table 2 is meant to indicate active measurement acquisition for the indicated sensing modality (i.e., field potential measurement, single unit activity measurement (or multi unit activity measurement), and an optical measurement modality). The white background in the bottom two rows of Table 2 is meant to indicate no active acquisition for the indicated modality (i.e., voltammetry and rheoencephalography).

Continuous Acquisition with Electrical Stimulation Therapy Delivery

In some embodiments, a multimodal brain sensing lead not only may be configured to enable the acquisition of physiological information from the patient using two or more different sensing modalities but also may be configurable to deliver a form of therapy to the patient. For example, when a multimodal brain sensing lead is used as part of an implantable responsive neurostimulation system, one or more of the sensing modalities may be used to acquire information from the patient that is then processed by an implanted neurostimulator to determine whether and, if so, when it might be appropriate to deliver a therapy to the patient in response to the acquired information. One type of the therapy the implant might determine is appropriate is a form of electrical stimulation (e.g., one or more bursts of pulsatile current-controlled or voltage-controlled stimulation). One or more components of the multimodal brain sensing lead may be used in delivering therapy to the patient. For example, one or more of the macroelectrodes on a multimodal brain sensing lead may be used to deliver the bursts of electrical stimulation when the implanted neurostimulator determines an epileptic seizure might be imminent based on the acquired information.

In this situation, the implanted neurostimulator may be configured to deliver stimulation for 1 second. With reference to FIG. 21B, Table 3 indicates that acquisition of measurements in the field potential measurement modality and the single unit activity measurement (or multi unit activity measurement) modality are suspended while electrical stimulation is delivered so that sensing amplifiers associated with acquiring measurements in those sensing modalities are not overwhelmed (e.g., saturated). The dotted background in the top three rows of Table 3 is meant to indicate active measurement acquisition for the indicated sensing modality. The white background in Table 3 is meant to indicate no active acquisition for the indicated modality. The cross-hatched background in the left-hand side of Table 3 for the field potential (FP) and single unit activity/multi unit activity (SUA/MUA) rows is meant to indicate that the acquisition of measurements in those modalities is suspended while electrical stimulation is being delivered (the time span associated with the cross-hatched area is meant to correspond to the one-second stimulation time).

Uses of Measurements Acquired from the Different Sensing Modalities

Multimodal measurements acquired using a multimodal brain sensing lead according to embodiments may be used in at least two general ways. One of these ways is to use the acquired data to visualize multiple physiological variables over time. Another is to use the acquired data to trigger therapy delivery by a therapy delivery device or device(s), such as in a closed-loop therapy delivery system.

Data Visualization

An example of how information acquired from a multimodal brain sensing lead according to embodiments might be visualized by a user of an implantable medical device system that includes the lead was previously described with reference to FIG. 16, as well as Table 4. FIG. 16 is a series of graphs tracking signals corresponding to measurements acquired in each of five different sensing modalities over a common time window (in this case, five days). It will be appreciated that a user's being able to visualize data acquired from different sensing modalities and from a localized region of the patient's brain over the same time period may be quite useful, for example, in initially diagnosing a patient or in evaluating the relative success of a particular treatment or therapy (e.g., drugs, electrical stimulation therapy, etc.). This sort of data visualization may reveal complicated combinations of physiological patterns that otherwise would be unobservable. The combinations of patterns may indicate physiological events or states occurring in the patient which the patient's treating physician previously did not fully appreciate. Thus, the physician's ability to easily comprehend these combinations of patterns of the data acquired from embodiments of a multimodal brain sensing lead may prompt the physician to try a type or form of clinical intervention than he or she otherwise would not have been prompted to try.

Table 4 represents one way of summarizing the data shown graphically in FIG. 16. A set of "events" labeled event "A", event "9", and event "C" are denoted in each of FIG. 16 and Table 4. In Table 4, an arrow pointing up is meant to indicate an increase in the measure of the relevant modality (e.g., an increase in the absolute value of a field potential or the increase in the optical blood volume compared to a long term or short term trend). An arrow pointing down is meant to indicate a decrease in the measure of the relevant modality.

TABLE 4

| Sensing Modality | A | B | C |
|---|---|---|---|
| Field Potential Measurement (summarizes graph 1602 of FIG. 16) | | ▲ | ▲ |
| Single Unit Activity Measurement or Multi Unit Activity Measurement (summarizes graph 1604 of FIG. 16) | ▲ | ▲ | |
| Optical Measurement (e.g., Optical Blood Volume or Optical Blood Oxygenation Measurement) (summarizes graph 1606 of FIG. 16) | | | ▲▼ |
| Voltammetry Measurement (summarizes graph 1608 of FIG. 16) | ▲ | ▲ | |
| Rheoencephalography Measurement (summarizes graph 1610 of FIG. 16) = | ▼ | | ▼ |

▼ = decrease,
▲ = increase

Multimodal data visualization is very information rich, and therefore is likely to provide a much more comprehensive and superior representation of physiological changes over time than is data acquired using only a single sensing modality (such as field potential measurement modality) or than is data acquired using multiple modalities but from different probes in contrast to the highly localized information that can be obtained when multiple different sensing modalities are implemented on a single brain sensing lead.

FIG. 16 and Table 2 illustrate several examples. Each modality in FIG. 16 exhibits a main broad peak and trough each day, along with superimposed irregularities that may be indicative of a physiological event. Table 4 summarizes the irregularities and departures from the underlying circadian rhythm for each modality. First, a circadian rhythm may be observed when the data over five days from all five of the represented modalities is appreciated, even though data from no single one of the represented modalities might unambiguously reflect such a circadian rhythm. In other words, when data from all five modalities acquired over the same live days is viewed collectively, it seems apparent that fluctuations in the measurements occur at different times of day. Second, it may be observed that events "A", event "B", and event "C" are distinguishable from each other across modalities, but are not necessarily distinguishable from each other within the confines of data acquired using a single one of the different sensing modalities. For example, if one considers event "B" in Table 4 (corresponding to the information acquired from a field potential measurement sensing modality) and compares it to event "C" in that same row of Table 4, they appear the same because they both show an increase. However, when one looks at the changes in the signals in Table 4 for all five sensing modalities, then it can be appreciated that event "B" is characterized by different features than is event "C": for example, single unit activity or multi unit activity increases during event "B" but does not change during event C.

Similarly, if one compares event "A" to event "B" in Table 4 with respect to the single unit activity measurement modality (or the multi unit activity measurement modality), both events show increases and no dramatic differences are apparent. However, when one looks at the nature of the signal in all five sensing modalities in Table 4, then it can be appreciated that event "A" is characterized by different features than is event "B": for example, the field potential measurement does not change during event "A" but increases during event "B", and the rheoencephalography measurement decreases during event "A" but does not change during event "B".

Closed Loop Therapy Delivery System

As previously discussed herein, for example with reference to FIGS. 17, 19, and 20, multimodal brain sensing leads according to embodiments may be used beneficially with an implantable medical device system that has a feature for delivering therapy based on feedback sensed from the patient related to one or more conditions of the patients. A responsive neurostimulation system is a particular example of such a closed-loop therapy delivery system, in which sensed information (such as from a patient with epilepsy) is processed by an implantable neurostimulator and subjected to one or more detection algorithms running on the implantable neurostimulator to detect patterns and/or sequences occurring in the sensed signals, and when a pattern and/or sequence is detected, the neurostimulator "responds" by generating and then delivering a form of electrical stimulation therapy (perhaps through the same electrodes that are used to sense information from the patient in the first instance).

In particular, FIG. 17 and its accompanying description (above) illustrate an example of how data acquired from two or more different sensing modalities implemented on a multimodal brain sensing lead according to embodiments may be used in a closed-loop feedback therapy delivery system.

Clinical Examples

Embodiments of the multimodal brain sensing lead may be used, with other components of an implantable medical device system such as a responsive neurostimulation system or with components of other types of systems such as systems having all but the lead component external of the patient, in a variety of clinical contexts. Some examples of clinical contexts include epilepsy, major depression, and Parkinson's disease. Some of these contexts are described briefly below.

Epilepsy Examples

Epilepsy patients experience seizures, which typically are accompanied by abnormal electrographic activity, blood flow changes, tissue oxygenation changes, and neurotransmitter changes. Often, seizures begin in a specific area of the brain called the seizure focus. The location of the seizure focus varies from patient to patient and an individual patient may have multiple seizure foci. Physiological monitoring of the seizure focus can provide important diagnostic information, especially the timing of changes in physiological variables. For example, seizures often may be characterized by a transition from baseline to epileptiform EEG waveforms and are often preceded by decreases in blood flow at the seizure focus.

In an example, a patient visits a doctor because he has begun having seizures. The doctor admits the patient to the hospital epilepsy monitoring unit (EMU) and has scalp electroencephalography (EEG) recordings performed. Based on the scalp EEG data, the doctor suspects the patient has seizures coming from the left anterior hippocampus of the temporal lobe. An intracranial EEG (iEEG) recording lead is implanted (acutely) in the left anterior hippocampus to confirm the location of the seizure focus and count seizures. The data from this diagnostic procedure shows nearly constant abnormal epileptiform electrographic activity in the anterior hippocampus, making it difficult if not nearly impossible to distinguish seizures from background activity.

Being able to count seizures and measure the seizure rate is important in assessing a patient's condition and the effect of any treatments. A doctor familiar with the literature describing changes in blood flow and oxygenation during seizures may decide to use an embodiment of a multimodal brain sensing lead such as described herein to monitor both iEEG activity and hemodynamic changes, with the expectation that this will provide better information than iEEG activity alone.

To measure changes in physiological variables corresponding to the iEEG activity and the hemodynamic changes, the doctor surgically implants a multimodal brain sensing lead configured with components enabling acquisition of measurements for at least two different sensing modalities, namely, the neuronal field potential measurement modality and an optical sensing modality (e.g., the optical blood volume measurement modality or the optical blood oxygenation measurement modality). The multimodal brain sensing lead is stereotactically implanted into the patient so that a distal portion thereof is situated at or near the suspected seizure focus in the anterior hippocampus. More specifically, in this particular scenario, the distal portion of the multimodal brain sensing lead is implanted in the patient's anterior hippocampus. A proximal portion of the lead is left external of the patient so that it can be connected to an external host device.

After recovery from surgery, the patient is returned to the Epilepsy Monitoring Unit (EMU). In the EMU, the proximal portion of the lead is connected to an external host device, in this case a small computer with custom hardware and software necessary to connect to, communicate with, configure, and collect data acquired using the components for the sensing modalities provided in the implanted multimodal brain sensing lead. The system including the lead is then configured for collecting field potential and hemodynamic measurements.

Neuronal field potential recording is used to record iEEG activity including electrographic spikes, waves and oscillatory activity from neurons near the macroelectrodes on the multimodal lead. Some methods by which field potential measurements might be acquired using a multimodal brain sensing lead according to embodiments has been described in some detail previously herein. However, when the multimodal brain sensing lead is being used in a diagnostic procedure, for example, in an EMU with an external host device receiving and processing signals sensed from the implanted lead, the methods may be adjusted to, for example, address the presence of electromagnetic noise generated by other equipment in the patient's hospital environment.

In an example, two separate field potential channels are configured for differential recording. The field potential amplifiers (designated as the field potential amplifier #1 and the field potential amplifier #2 in this example) are located in the host device and not in the lead. Differential recording is selected to minimize electromagnetic noise from equipment in the room, and to help localize the seizure focus. Differential mode also is selected because a field potential signal describing differences between neural activities at two macroelectrodes is desired. This signal will reflect primarily activity near the electrodes and subtract out background activity common to both electrodes.

There are four macroelectrodes (designated the first, second, third and fourth macroelectrodes in this example) available for field potential recording. A pair of macroelectrodes is selected to provide the inputs to each differential amplifier. The field potential amplifier #1 is configured for differential recording using the first and second macroelectrodes, the most distal electrodes, as inputs. This results in a differential field potential signal that describes population neuronal activity near macroelectrodes #1 and #2 at the distal end of the lead. The field potential amplifier #2 is also configured for differential recording but using the more proximal third and fourth macroelectrodes as amplifier inputs. This results in a differential field potential signal that describes population neuronal activity near the third and fourth macroelectrodes in an area adjacent to and more proximal than the first and second macroelectrodes. If the seizure focus is closer to the first and second macroelectrodes, then the seizure signal will be larger on the output of field potential amplifier #1. If the seizure focus is closer to the third and fourth macroelectrodes, then the seizure signal will be larger on the output of the field potential amplifier #2.

Next, filter settings are selected. These field potential amplifier channels will be used primarily for recording in the standard delta to gamma EEG frequency range, approximately 3 to 100 Hz. A high-pass filter is set at 1 Hz, and a low-pass filter is set at 125 Hz. These settings are typical for field potential recording. A 60 Hz notch filter is enabled because power line noise is expected to be present. Next, a gain setting is selected. For this channel, a gain of 100 is selected because field potential voltage spikes of approximately ±10 mV are expected. This will result in approximately ±1 V output from the amplifier. This is within the amplifier's dynamic range, assuming the amplifier is powered with 3.5 V. Finally, a sampling rate, the rate at which the analog voltage measurements are converted to digital values, of 250 samples per second is selected. This sampling rate is sufficient for EEG field potential recording in the 3-100 Hz range.

After the host amplifiers and filters are configured, continuous iEEG field potential data collection is started. While field potential data are being collected, digitized voltage measurements are continuously stored in the host device at a rate of 250 samples per second for each amplifier channel. Field potential data are stored in data files on the host storage medium, which may be RAM memory or a hard drive.

Optical recording is used to measure blood flow, blood pressure, blood oxygenation, heart rate, and breathing rate. The host device operates together with the optical sensing elements on the multimodal lead to make optical measurements. The optical sensing elements on the multimodal lead consist of four 805 nm light emitting diodes (LEDs), four 630 nm LEDs, four photodiodes (PDs), one switched-capacitor (SC) amplifier, and one analog-to-digital converter (ADC). The external host device controls measurement acquisition by sending control signals through the two control wires of the lead.

The iEEG field potential and hemodynamic optical data stored in the external host device are used to identify and characterize seizures. The iEEG field potential signal shows many long epileptiform discharges but the doctor may be uncertain as to which ones are seizures. So, the doctor may use acquired optical signals using one or more of the optical sensing modalities of the multimodal brain sensing lead to help identify real seizures. The doctor may appreciate that the patient's breathing, heart rate, and blood pressure are likely to increase during seizures. The doctor may further appreciate that blood flow in the seizure focus increases during a seizure and may decrease before the seizure. The doctor also may understand that blood oxygenation briefly decreases at the onset of a seizure, then increases, then decreases again. Thus, in order to identify clinical seizures, the doctor may look for the presence of as many of these seizure patterns as possible in the signals obtained from the multimodal brain sensing lead. If the doctor observes that field potential channel #1 shows epileptiform discharges that correlate with breathing rate, heart rate and blood pressure increases from one or more of the optical assemblies on the lead that is being used to acquire data in an optical measurement modality or modalities (e.g., to assess blood flow and oxygenation changes).

Based on these observations, the doctor may be able to identify and count the patient's clinical seizures. The doctor further may be able to use this information to assess the effects of the epilepsy treatments to which the patient is or may be subjected (e.g., electrical stimulation therapy).

The data acquired from a multimodal brain sensing lead according to embodiments also may be used to determine which sensors and which signals from those sensors are likely to provide consistently) the highest quality and most clinically relevant information. The highest quality signals may be defined as those which have the highest signal-to-noise ratio and the fewest artifacts. The most clinically relevant signals may be defined as those which are most highly correlated with physiological states and events of interest, such as seizures. For example, if a signal does not vary appreciably with seizures, it likely is not clinically relevant to the patient's epilepsy. On the other hand, signals that change dramatically during seizures are likely to be very clinically relevant.

These multimodal data may also be used for other purposes in epilepsy patients. If particular multimodal physiological patterns tend to occur prior to seizures, then the multimodal information may be used by the host device to alert the patient or a caregiver that a seizure is likely to occur, in this case, the patient or caregiver may be instructed or otherwise signaled to administer an antiepileptic treatment such as an oral drug that would reduce the likelihood or prevent the seizure from occurring. An additional use for the multimodal information may be to detect Sudden Unexplained Death in Epilepsy (SUDEP) Imminent SUDEP would be indicated by cessation of cardiac activity and respiration and possibly dramatic changes in electrographic activity. The host device may be configured to alert patient caregivers in this situation so that they may attempt to treat or revive the patient.

Major Depression

Abnormal blood flow in the frontal lobes is believed to be associated with major depression. Abnormal blood flow can be measured using optical sensing or rheoencephalography. It is likely that electrographic changes are also associated with depression symptoms. These changes can be measured using either macroelectrodes or microelectrodes. There are also neurotransmitter changes associated with depression, especially in the serotonergic system. An example of a clinical application of a multimodal brain sensing lead according to embodiments in major depression would include implanting a multimodal depth brain sensing lead so that a distal portion thereof is in the vicinity of Area 25 or the anterior limb of the interior capsule/nucleus accumbens (ALIC/NA). The multimodal brain sensing lead may be configured so that each of the field potential measurement modality, the single unit activity or multi unit activity measurement modality, the optical measurement modality (blood volume and/or blood oxygenation), and the rheoencephalography modalities are available. Once the lead is implanted, multiple different ones of the available sensing modalities can be used to acquire information from which estimates of blood flow, optical blood volume and variables related to rheoencephalography can be made (e.g., in a host device or manually by the physician). The field potential measurement modality and the single unit activity measurement (or multi unit measurement) modality may be availed upon to measure electrographic changes and to record action potential behavior at the level of a single neuron or at the level of a small group of neurons.

The multimodal depth lead can be used in the following manner for treating major depression. First, the lead is implanted in an area of the brain expected to exhibit symptoms correlated with affective changes in major depression. Examples of target areas include but are not limited to Area 25 and the ALIC/NA. The multimodal lead would be connected to a host device. The host device would serve to power and control the multimodal lead, and to process and store signals received from the lead, and to communicate with other external devices including but not limited to wireless telemetry transceivers connected to external computing platforms. Examples of the host device include but are not limited to a small host device implanted in a surgically created defect of the patient's skull, or an external host device such as a computer. Together, the host device and the multimodal lead collect multimodal measurements using an interleaved timing scheme that repeats at scheduled intervals. The scheduled interval is configured to provide a time-series record of physiological measurements that has sufficient temporal resolution to detect clinically meaningful physiological changes related to the patient's disease state. The sampling interval may be different for each modality, and may vary depending on the patient's physiological state as detected by the host-lead system. For example, the sampling interval for all of the modalities may be one sample per second, one sample per minute, one sample per hour, or vary between sensing modalities. For example, optical blood flow measurements could be one per minute while the macroelectrode neuronal field potential measurements could be 200 samples per second.

Importantly, voltammetry measurements may be used to measure either neurotransmitter levels, such as serotonin, dopamine, norepinephrine, or levels of therapeutic drugs such as serotonergic or dopaminergic pharmaceuticals. Thus, data acquired using a voltammetry sensing modality can be used to provide a view of neurotransmitter and drug fluctuations over time, which can aid a physician in prescribing and adjusting treatment drugs In sum, data from a multimodal brain sensing lead may also be used beneficially, in conjunction with another component or components configured to process and analyze the data (e.g., an external host device or an implanted host device as part of an implantable medical device system), in an application to diagnose and treat a patient experiencing a depressive disorder. The lead may be used in this manner to accurately diagnose the patient's clinical state and prescribe treatment. Diagnosis will be aided because a time series record of symptoms associated with depression will be available, as obtained from the local information acquired by the one or more sensing modalities implemented on the lead. In addition to subjective information elicited from the patient about his or her symptoms of depression, the physician can beneficially use objective evidence obtained from the different sensing modalities to determine such things as whether the patient is in a depressed state, if so, for how long the state has persisted; a continuous history of the patient's history of depressed states; the duration and severity of each state; and the intervals between depressed states. The physician will use this information to assess the patient's responses to treatment and to guide future treatment prescriptions.

In addition, when used in conjunction with a closed loop therapy delivery system, a multimodal brain sensing lead according to embodiments can be used to identify changes in physiological measures that may predict whether the patient will develop depression symptoms. Based on specific changes in the physiological measures, therapeutic interventions may be initiated so that depression symptoms do not develop. Such a prophylactic approach may also be used to administer therapies in order to maintain a desired physiological state so that therapy is provided only as often and to the extent that it is Deeded.

Parkinson's Disease

Embodiments of a multimodal brain sensing lead also may be used beneficially, in conjunction with another component or components configured to process and analyze the data (e.g., an external host device or an implanted host device as part of an implantable medical device system), to assess Parkinson's disease symptoms. Parkinson's disease is characterized by a loss of dopaminergic neurons in the substantia nigra (SN). This leads to abnormally high activity in the subthalamic nucleus (STN), which the substantia nigra normally inhibits through synaptic connections. Other brain areas that receive input from the substantia nigra and subthalamic nucleus also may show abnormal neural activity. Nearly all Parkinson's disease patients also take medications such as Sinemet (carbidopa-levodopa), the concentrations of which at or near the relevant structures in the patient's brain may be of interest to the treating physician.

A multimodal brain sensing lead according to embodiments may be used beneficially in a therapy for treating Parkinson's disease patients by implanting a distal portion of the lead in the subthalamic nucleus or another brain area and using it to monitor physiological variables and drug levels. In an example, a distal portion of a multimodal depth brain sensing lead is implanted in a subthalamic nucleus (STN). The lead is configured with several sensing modalities: the field potential sensing modality (i.e., to measure field potentials using macroelectrodes); the neuronal single unit activity measurement modality (and/or multi unit activity measurement modality) (i.e., to measure action potentials using microelectrodes); the voltammetry measurement modality (i.e., to measure neurotransmitter (e.g., dopamine) levels using the voltammetry components on the lead); the optical measurement modality (e.g., the optical blood volume measurement modality) (i.e., to estimate blood flow using the optical assembly(ies) on the lead. The single unit activity measurement modality and the multi unit measurement modality each may be expected to acquire data that show increased oscillatory activity in the beta frequency range when Parkinson's disease symptoms are present. The voltammetry sensor implemented by the relevant components on the lead may be expected to measure changes in Sinemet drug levels as blood levels of the drug increase after oral administration and then decrease as the drug is metabolized.

In this particular example, the multimodal brain sensing lead may be connected to an implanted host device that controls data acquisition and processes and stores measurement data. Electrophysiological measurements may be acquired at 200 samples per second. Optical measurements may be acquired at a rate of once per minute. Voltammetry measurements also may be acquired at a rate of once per minute. A treatment algorithm running in the host device may be configured to analyze the time-series of physiological measurements and then to use the time-series patterns to determine whether and, if so, when to deliver a therapy to the patient and according to what therapy parameters (or therapy settings), based on a pre-determined set of therapy settings defined by the physician. For example, when Sinemet blood levels are above a threshold pre-determined by the physician, a system including the multimodal brain sensing lead and the implanted host device may be configured to deliver pulsatile electrical stimulation through the macroelectrodes at a low level (e.g., 130 Hz, 160 microseconds per phase, biphasic square pulses with a 100 microsecond inter-phase interval, at 1 volt amplitude). The system may be programmed such that, if Sinemet blood levels exceed the threshold, the stimulation amplitude may be increased to 3 volts. Alternatively, the system could include a feature whereby different amplitude settings (including zero volts) are mapped to different Sinemet blood level ranges so that as the Sinemet blood level gradually decreases, the stimulation amplitude may be gradually increased, thus maintaining the combined therapeutic effect of Sinemet and stimulation. Additionally, when beta oscillations are observed (for example, by the implanted host device) as a result of measurements acquired from the multimodal brain sensing lead in either the multi unit activity measurement modality or the single unit activity measurement modality, and the beta oscillations are characterized by an amplitude and duration in excess of levels pre-determined by the physician, the implanted host device may be configured to increase the amplitude of the electrical stimulation to 3 volts until the data obtained from the lead sensors indicates that the beta oscillation subsides.

Closed Loop Therapy Delivery

As previously discussed herein, one or more multimodal brain sensing leads may be used as component(s) of a closed loop therapy delivery system. Such a system may trigger delivery of a therapy to the patient (or generation and delivery of a therapy to the patient) in response to the processing and analyze of data acquired from one or more of the sensing modalities implemented on the multimodal brain sensing lead(s). Alternatively or additionally, such a system may adjust a form of therapy automatically based on the information that is being acquired using one or more of the sensing modalities implemented on the multimodal brain sensing lead(s), for example, in real time.

Generally, the components of a closed loop therapy system may be configured to collect, process, store and analyze data acquired from one or more of the measurement modalities available on the multimodal brain sensing lead(s). For example, an algorithm running on a host device would use these data to determine when to deliver therapy and how much to deliver. Therapy may take the form of automatic drug delivery into the body from a drug pump, or neuromodulatory electrical stimulation through the macroelectrodes into the tissue surrounding the distal portion of the lead. For example, when a closed loop system detects decreased levels of blood flow and/or neurotransmitter levels (e.g., serotonin or dopamine), the system may be configured to automatically deliver a therapeutic dose of a serotonergic drug such as fluoxetine. Therapy may also take the form of electrical stimulation delivered through the macroelectrodes on the lead. The stimulation settings (i.e., electrode selection, waveform, polarity, pulse width, pulse frequency, pulse amplitude, current-controlled or voltage-controlled) may be predetermined by the physician. Different stimulation parameters could be selected by the physician to be delivered based on the physiological measurements processed and analyzed by the host device and/or based on the physician's assessment of those measurements when the results are displayed to the physician, for example, as a snapshot in time of the behavior of the neural tissue in the highly localized region of the brain in which the distal portion of the lead(s) is/are situated.

Examples of Host Devices

A host which accepts and processes and otherwise reacts to data obtained from multimodal brain sensing lead(s) according to embodiments may include an implantable responsive neurostimulator such as described below.

FIG. 19 illustrates one example of an implantable medical device system having both implantable and external components and with which multimodal brain sensing leads according to embodiments may be beneficially used. A host device 2006 is shown implanted in a patient 2024 (in this case, in the cranium of the patient). The host device 2006 may have various elements that allow it to process and analyze data acquired using the various sensing modalities of the multimodal brain sensing lead (e.g., a control module 2008, a power supply 2010 and a clock 2012). The host device further may have one or more elements that control the timing of the acquisition of data from one sensing modality as compared with another sensing modality. In addition, the host device may have elements that allow it to react to the data acquired from the various sensing modalities implemented on the multimodal brain sensing lead, such as by generating and delivering a burst or bursts of pulsatile electrical stimulation to the patient. In some implantable medical device systems, the multimodal brain sensing lead may include components such as macroelectrodes that can be used for sensing in one or more of the sensing modalities and also for delivering electrical stimulation to the patient as one reaction to data sensed from the lead.

Generally, the implantable host device 2006 of the implantable medical device system shown in FIG. 19 is able to detect neurological events (e.g., spatial or temporal patterns or sequences believed to correspond in some way to a patient's condition or disorder), record and/or log the neurological events in memory, and then communicate the data it acquires and the events it detects to one or more external components from which the data and event information can be used by a physician in further diagnosing or otherwise treating the patient. An implantable medical device system comprising a responsive neurostimulation system, for example, may be configurable to detect events that are understood to be related to some aspect of a patient's epilepsy, e.g., seizures, seizure onsets or precursors to seizures.

In a responsive neurostimulation system, the implanted neurostimulator, e.g., the host device 2006 in FIG. 19 may be configured to record neurological signals, such as electrocorticographic (ECoG) waveforms, to detect and analyze ECoG signals, and/or to create a log of such detection and analysis. (EEG signals represent aggregate neuronal activity potentials detectable via sensors applied to a patient's scalp. ECoG signals, which are deep-brain or cortical surface counterparts to the EEG signals, are detectable via sensors implanted on or under the dura mater, and usually within the patient's brain. Unless otherwise noted herein, the term "EEG" is used generically herein to refer to both EEG and ECoG signals, the ECoG signals generally being considered a subset of EEG signals.)

A responsive neurostimulator typically is programmable and typically has a relatively large number and variety of parameters that can be set and subsequently be modified in a programming session after the neurostimulator is implanted in a patient. When used to process and analyze signals obtained from the various measurement modalities implemented in a multimodal brain sensing lead according to embodiments, programming the neurostimulator may involve specifying parameter values that: will control signals that are generated and delivered to the distal portion of the lead necessary to acquire a given measurement for a given sensing modality; process signals that are received hack from the components used in the lead to implement the various modalities (e.g., amplifier gain settings or filter settings); and determine which patterns or sequences or combinations of the same will be determined to constituted "events" by the neurostimulator when they occur in the data acquired from the various sensing modalities implemented on the lead. Thus, for example, the responsive neurostimulator may be programmed to begin recording detected ECoG signals satisfying certain detection parameters or criteria (e.g., based on a combination of parameter values) from the patient 2024 at the onset or otherwise as a result of ictal activity. The responsive neurostimulator may be configured to record signals or values corresponding or related to signals at times before, during and after the detection criteria have been met. The responsive neurostimulator may be configured to continue recording until the ictal activity stops.

Optionally, the responsive neurostimulator 2006 saves relevant recordings, or sampling thereof, to a local memory in order to preserve it for later downloading to an external device, such as one of the programmers 2020A, 2020B, 2020C and 2020D or the patient remote monitor 2026 shown in FIG. 19. The responsive neurostimulator may also create a log of the events (e.g., ictal activity) that it records. In one example, the responsive neurostimulator records and/or logs the date and time when an event begins and ends, the duration of the event, indications of the intensity of the event, etc.

The responsive neurostimulator may also be configured to record and/or preserve data corresponding to ECoG signals upon the initiation of some action (e.g., swiping an external magnet near the site at which the responsive neurostimulator is implanted) by the patient, a caregiver or physician.

It should be appreciated that an implantable host device useful with a multimodal brain sensing lead according to embodiments may be configured to detect any kind of neurological condition or disorder that has a representative signature relative to data acquired from one of the available sensing modalities or relative to data acquired from some combination of the available sensing modalities, for example, in a certain window of time. While an implantable host device in the form of a responsive neurostimulator is described above, sometimes with reference to an epilepsy application, it should be appreciated that embodiments of the multimodal brain sensing lead may be useful with a great variety of host devices (implantable or external to the patient) for a great many applications. By way of example and not by way of limitation, the host device may be only configured as a diagnostic tool, and therefore may not have any capacity to react to data acquired from a sensing modality implemented on the lead with a therapy. The host device may be used with embodiments of the multimodal brain sensing lead in applications relevant to almost any conceivable neurological condition or disorder, including but not limited to studies and therapies relating to epilepsy, movement disorders, psychiatric disorders, headaches, obesity, gastroenterological disorders, stroke recovery, Alzheimer's disease, and so on and so forth. The richness of the information about localized regions of a patient's brain that can be obtained using embodiments of the multimodal brain sensing lead is expected to better inform diagnosis and treatment for many diverse and complex disorders and conditions.

Various example embodiments are thus described. All statements herein reciting principles, aspects, and embodiments as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope, therefore, is not intended to be limited to the embodiments shown and described herein.

What is claimed is:

1. An implantable medical device comprising:
    a lead comprising:
        a cylindrical lead body having a distal portion configured to be implanted in or on a brain and a proximal portion; and
        a plurality of lead components at the distal portion, wherein the plurality of lead components includes a plurality of macroelectrodes, a plurality of microelectrodes, and at least one optical sensor assembly, and are configured to implement a plurality of different sensing modalities; and
    a host device coupled to the lead and operating in accordance with a timing schedule to implement time multiplexed continuous measurement acquisition during which at least one of the different sensing modalities is implemented to obtain a corresponding measurement, wherein the timing schedule suspends implementation of a first sensing modality during implementation of a second sensing modality, wherein the host device controls the lead to implement at least two different sensing modalities that share a same type of lead component.

2. The implantable medical device of claim 1, wherein the plurality of macroelectrodes are spaced apart along a length of the distal portion of the lead body, and the plurality of microelectrodes are spaced apart around a circumference of the distal portion of the lead body.

3. The implantable medical device of claim 2, wherein the circumference around which the plurality of microelectrodes are spaced is located along the length of the distal portion of the lead between a pair of the plurality of macroelectrodes.

4. The implantable medical device of claim 1, wherein the plurality of macroelectrodes are spaced apart along a length of the distal portion of the lead body, and the at least one optical sensor assembly is located along the length of the distal portion of the lead between a pair of the plurality of macroelectrodes.

5. The implantable medical device of claim 1, wherein:
the host device implements continuous measurement acquisition through host control signals; and
the lead further comprises an electronics module configured to receive the host control signals and to selectively enable, based on the host control signals, one of the plurality of different sensing modalities.

6. The implantable medical device of claim 1, wherein:
the first sensing modality corresponds to a field potential measurement that is implemented by at least one of the plurality of macroelectrodes; and
the second sensing modality corresponds to a rheoencephalography measurement that is implemented by at least one of the plurality of macroelectrodes.

7. The implantable medical device of claim 1, wherein:
the first sensing modality corresponds to a single unit activity measurement that is implemented by at least one of the plurality of microelectrodes; and
the second sensing modality corresponds to a voltammetry measurement that is implemented by at least one of the plurality of microelectrodes.

8. The implantable medical device of claim 1, wherein:
the first sensing modality corresponds to a multi unit activity measurement that is implemented by at least one of the plurality of microelectrodes; and
the second sensing modality corresponds to a voltammetry measurement that is implemented by at least one of the plurality of microelectrodes.

9. The implantable medical device of claim 1, wherein:
one of the plurality of different sensing modalities corresponds to one of optical blood volume and optical blood oxygenation implemented by the at least one optical assembly; and
the timing schedule implements the one of optical blood volume and optical blood oxygenation continuously.

10. The implantable medical device of claim 1, wherein:
the host device is further configured to output an electrical stimulation signal to one or more of the macroelectrodes;
the first sensing modality corresponds to a field potential measurement that is implemented by at least one of the plurality of macroelectrodes; and
the timing schedule is configured to suspend implementation of the first sensing modality during electrical stimulation output.

11. The implantable medical device of claim 1, wherein:
the host device is further configured to output an electrical stimulation signal to one or more of the macroelectrodes;
the first sensing modality corresponds to a single unit activity measurement that is implemented by at least one of the plurality of macroelectrodes; and
the timing schedule is configured to suspend implementation of the first sensing modality during electrical stimulation output.

12. The implantable medical device of claim 1, wherein:
the host device is further configured to output an electrical stimulation signal to one or more of the macroelectrodes;
the first sensing modality corresponds to a multi unit activity measurement that is implemented by at least one of the plurality of macroelectrodes; and
the timing schedule is configured to suspend implementation of the first sensing modality responsive to electrical stimulation output.

* * * * *